(12) United States Patent
Santos

(10) Patent No.: US 8,252,282 B2
(45) Date of Patent: Aug. 28, 2012

(54) NUCLEAR TELOMERASE REVERSE TRANSCRIPTASE VARIANT

(75) Inventor: Janine H. Santos, Dunellen, NJ (US)

(73) Assignee: University of Medicine & Dentistry of New Jersey, Somerset, NJ (US)

( * ) Notice: Subject to any disclaimer, the term of this patent is extended or adjusted under 35 U.S.C. 154(b) by 548 days.

(21) Appl. No.: 12/456,593

(22) Filed: Jun. 18, 2009

(65) Prior Publication Data

US 2010/0003229 A1  Jan. 7, 2010

Related U.S. Application Data

(60) Provisional application No. 61/132,673, filed on Jun. 19, 2008.

(51) Int. Cl.
*A61K 38/43* (2006.01)
(52) U.S. Cl. ...................................................... 424/94.1
(58) Field of Classification Search .................. 424/94.1
See application file for complete search history.

(56) References Cited

U.S. PATENT DOCUMENTS

| 6,475,789 | B1 | 11/2002 | Cech et al. |
| 6,610,839 | B1 | 8/2003 | Morin et al. |
| 7,199,234 | B2 | 4/2007 | Morin et al. |

OTHER PUBLICATIONS

Seimiya et al. "Involvement of 14-3-3 proteins in nuclear localization of telomerase", The EMBO Journal, 2000, 19(11):2652-2661.*
Santos et al. "Mitochondrial hTERT exacerbates free-radical-mediated mtDNA damage", Aging Cell, 2004, 3:399-411.*

* cited by examiner

*Primary Examiner* — Sue Liu
*Assistant Examiner* — Bin Shen
(74) *Attorney, Agent, or Firm* — Licata & Tyrrell P.C.

(57) ABSTRACT

The present invention is directed to a novel variant of human telomerase reverse transcriptase (S16AhTERT), which displays properties distinct from those of wildtype telomerase reverse transcriptase. Accordingly, the amino acid sequence of S16AhTERT and nucleic acid sequences encoding same are presented herein, as are methods of use thereof.

9 Claims, 2 Drawing Sheets

MPRAPRCRAVRSLLRsHYRE (SEQ ID NO: 5): Wild type

MPRAPRCRAVRSLLRaHYRE (SEQ ID NO: 6): S16A

SEQUENCE LISTING

<160> NUMBER OF SEQ ID NOS: 6

<210> SEQ ID NO 1
<211> LENGTH: 3396
<212> TYPE: DNA
<213> ORGANISM: Homo sapiens

<400> SEQUENCE: 1

```
atgccgcgcg ctccccgctg ccgagccgtg cgctccctgc tgcgcgccca ctaccgcgag      60
gtgctgccgc tggccacgtt cgtgcggcgc ctggggcccc agggctggcg gctggtgcag     120
cgcggggacc cggcggcttt ccgcgcgctg gtggcccagt gcctggtgtg cgtgccctgg     180
gacgcacggc cgcccccgc cgcccctcc ttccgccagg tgtcctgcct gaaggagctg     240
gtggcccgag tgctgcagag gctgtgcgag cgcggcgcga agaacgtgct ggccttcggc     300
ttcgcgctgc tggacggggc ccgcggggc cccccgagg ccttcaccac cagcgtgcgc     360
agctacctgc caacacggt gaccgacgca ctgcggggga gcggggcgtg ggggctgctg     420
ctgcgccgcg tgggcgacga cgtgctggtt cacctgctgg cacgctgcgc gctctttgtg     480
ctggtggctc ccagctgcgc ctaccaggtg tgcgggccgc cgctgtacca gctcggcgct     540
gccactcagg cccggccccc gccacacgct agtggacccc gaaggcgtct gggatgcgaa     600
cgggcctgga accatagcgt cagggaggcc ggggtccccc tgggcctgcc agccccgggt     660
gcgaggaggc gcggggcag tgccagccga agtctgccgt tgcccaagag gcccaggcgt     720
ggcgctgccc ctgagccgga gcggacgccc gttgggcagg ggtcctgggc ccacccgggc     780
aggacgcgtg gaccgagtga ccgtggtttc tgtgtggtgt cacctgccag acccgccgaa     840
gaagccacct ctttggaggg tgcgctctct ggcacgcgcc actcccaccc atccgtgggc     900
cgccagcacc acgcgggccc cccatccaca tcgcggccac cacgtccctg ggacacgcct     960
tgtcccccgg tgtacgccga gaccaagcac ttcctctact cctcaggcga caaggagcag    1020
ctgcggccct ccttcctact cagctctctg aggcccagcc tgactggcgc tcggaggctc    1080
gtggagacca tctttctggg ttccaggccc tggatgccag ggactccccg caggttgccc    1140
cgcctgcccc agcgctactg gcaaatgcgg cccctgtttc tggagctgct tgggaaccac    1200
gcgcagtgcc cctacggggt gctcctcaag acgcactgcc cgctgcgagc tgcggtcacc    1260
ccagcagccg gtgtctgtgc ccgggagaag ccccagggct ctgtggcggc ccccgaggag    1320
gaggacacag accccgtcg cctggtgcag ctgctccgcc agcacagcag ccctggcag    1380 gtgtacggct tcgtgcgggc ctgcctgcgc cggctggtgc ccccaggcct ctggggctcc    1440
aggcacaacg aacgccgctt cctcaggaac accaagaagt tcatctccct ggggaagcat    1500
gccaagctct cgctgcagga gctgacgtgg aagatgagcg tgcgggactg cgcttggctg    1560
cgcaggagcc caggggttgg ctgtgttccg gccgcagagc accgtctgcg tgaggagatc    1620
ctggccaagt tcctgcactg gctgatgagt gtgtacgtcg tcgagctgct caggtctttc    1680
```

```
ttttatgtca cggagaccac gtttcaaaag aacaggctct ttttctaccg gaagagtgtc   1740
tggagcaagt tgcaaagcat tggaatcaga cagcacttga agagggtgca gctgcgggag   1800
ctgtcggaag cagaggtcag gcagcatcgg gaagccaggc ccgccctgct gacgtccaga   1860
ctccgcttca tccccaagcc tgacgggctg cggccgattg tgaacatgga ctacgtcgtg   1920
ggagccagaa cgttccgcag agaaaagagg gccgagcgtc tcacctcgag ggtgaaggca   1980
ctgttcagcg tgctcaacta cgagcgggcg cggcgccccg gcctcctggg cgcctctgtg   2040
ctgggcctgg acgatatcca cagggcctgg cgcaccttcg tgctgcgtgt gcgggcccag   2100
gacccgccgc ctgagctgta ctttgtcaag gtggatgtga cgggcgcgta cgacaccatc   2160
ccccaggaca ggctcacgga ggtcatcgcc agcatcatca accccagaa cacgtactgc    2220 gtgcgtcggt atgccgtggt ccagaaggcc gcccatgggc acgtccgcaa ggccttcaag   2280
agccacgtct ctaccttgac agacctccag ccgtacatgc gacagttcgt ggctcacctg   2340
caggagacca gcccgctgag ggatgccgtc gtcatcgagc agagctcctc cctgaatgag   2400
gccagcagtg gcctcttcga cgtcttccta cgcttcatgt gccaccacgc cgtgcgcatc   2460
aggggcaagt cctacgtcca gtgccagggg atcccgcagg gctccatcct ctccacgctg   2520
ctctgcagcc tgtgctacgg cgacatggag aacaagctgt tgcggggat cggcgggac    2580 gggctgctcc tgcgtttggt ggatgatttc ttgttggtga cacctcacct cacccacgcg   2640
aaaaccttcc tcaggaccct ggtccgaggt gtccctgagt atggctgcgt ggtgaacttg   2700
cggaagacag tggtgaactt ccctgtagaa gacgaggccc tgggtggcac ggcttttgtt   2760
cagatgccgg cccacggcct attcccctgg tgcggcctgc tgctggatac ccggaccctg   2820
gaggtgcaga gcgactactc cagctatgcc cggacctcca tcagagccag tctcaccttc   2880
aaccgcggct tcaaggctgg gaggaacatg cgtcgcaaac tctttggggt cttgcggctg   2940
aagtgtcaca gcctgtttct ggatttgcag gtgaacagcc tccagacggt gtgcaccaac   3000
atctacaaga tcctcctgct gcaggcgtac aggtttcacg catgtgtgct gcagctccca   3060
tttcatcagc aagtttggaa gaaccccaca tttttcctgc gcgtcatctc tgacacggcc   3120
tccctctgct actccatcct gaaagccaag aacgcaggga tgtcgctggg ggccaagggc   3180
gccgccggcc ctctgccctc cgaggccgtg cagtggctgt gccaccaagc attcctgctc   3240
aagctgactc gacaccgtgt cacctacgtg ccactcctgg ggtcactcag gacagcccag   3300
acgcagctga gtcggaagct cccggggacg acgctgactg ccctggaggc cgcagccaac   3360
ccggcactgc cctcagactt caagaccatc ctggac                             3396
```

<210> SEQ ID NO 2
<211> LENGTH: 1132
<212> TYPE: PRT
<213> ORGANISM: Homo sapiens

<400> SEQUENCE: 2

```
Met Pro Arg Ala Pro Arg Cys Arg Ala Val Arg Ser Leu Leu Arg Ala
 1               5                  10                  15

His Tyr Arg Glu Val Leu Pro Leu Ala Thr Phe Val Arg Arg Leu Gly
             20                  25                  30

Pro Gln Gly Trp Arg Leu Val Gln Arg Gly Asp Pro Ala Ala Phe Arg
         35                  40                  45

Ala Leu Val Ala Gln Cys Leu Val Cys Val Pro Trp Asp Ala Arg Pro
     50                  55                  60

Pro Pro Ala Ala Pro Ser Phe Arg Gln Val Ser Cys Leu Lys Glu Leu
```

```
            65                  70                  75                  80
        Val Ala Arg Val Leu Gln Arg Leu Cys Glu Arg Gly Ala Lys Asn Val
                        85                  90                  95

Leu Ala Phe Gly Phe Ala Leu Leu Asp Gly Ala Arg Gly Gly Pro Pro
                        100                 105                 110

Glu Ala Phe Thr Thr Ser Val Arg Ser Tyr Leu Pro Asn Thr Val Thr
                        115                 120                 125

Asp Ala Leu Arg Gly Ser Gly Ala Trp Gly Leu Leu Arg Arg Val
                        130                 135                 140

Gly Asp Asp Val Leu Val His Leu Leu Ala Arg Cys Ala Leu Phe Val
        145                 150                 155                 160

Leu Val Ala Pro Ser Cys Ala Tyr Gln Val Cys Gly Pro Pro Leu Tyr
                        165                 170                 175

Gln Leu Gly Ala Ala Thr Gln Ala Arg Pro Pro His Ala Ser Gly
                        180                 185                 190

Pro Arg Arg Arg Leu Gly Cys Glu Arg Ala Trp Asn His Ser Val Arg
                        195                 200                 205

Glu Ala Gly Val Pro Leu Gly Leu Pro Ala Pro Gly Ala Arg Arg
                        210                 215                 220

Gly Gly Ser Ala Ser Arg Ser Leu Pro Leu Pro Lys Arg Pro Arg Arg
        225                 230                 235                 240

Gly Ala Ala Pro Glu Pro Glu Arg Thr Pro Val Gly Gln Gly Ser Trp
                        245                 250                 255

Ala His Pro Gly Arg Thr Arg Gly Pro Ser Asp Arg Gly Phe Cys Val
                        260                 265                 270

Val Ser Pro Ala Arg Pro Ala Glu Glu Ala Thr Ser Leu Glu Gly Ala
                        275                 280                 285

Leu Ser Gly Thr Arg His Ser His Pro Ser Val Gly Arg Gln His His
                        290                 295                 300

Ala Gly Pro Pro Ser Thr Ser Arg Pro Pro Arg Pro Trp Asp Thr Pro
        305                 310                 315                 320

Cys Pro Pro Val Tyr Ala Glu Thr Lys His Phe Leu Tyr Ser Ser Gly
                        325                 330                 335

Asp Lys Glu Gln Leu Arg Pro Ser Phe Leu Leu Ser Ser Leu Arg Pro
                        340                 345                 350

Ser Leu Thr Gly Ala Arg Arg Leu Val Glu Thr Ile Phe Leu Gly Ser
                        355                 360                 365

Arg Pro Trp Met Pro Gly Thr Pro Arg Arg Leu Pro Arg Leu Pro Gln
        370                 375                 380

Arg Tyr Trp Gln Met Arg Pro Leu Phe Leu Glu Leu Leu Gly Asn His
        385                 390                 395                 400

Ala Gln Cys Pro Tyr Gly Val Leu Leu Lys Thr His Cys Pro Leu Arg
                        405                 410                 415

Ala Ala Val Thr Pro Ala Ala Gly Val Cys Ala Arg Glu Lys Pro Gln
                        420                 425                 430

Gly Ser Val Ala Ala Pro Glu Glu Asp Thr Asp Pro Arg Arg Leu
                        435                 440                 445

Val Gln Leu Leu Arg Gln His Ser Ser Pro Trp Gln Val Tyr Gly Phe
                        450                 455                 460

Val Arg Ala Cys Leu Arg Arg Leu Val Pro Pro Gly Leu Trp Gly Ser
        465                 470                 475                 480

Arg His Asn Glu Arg Arg Phe Leu Arg Asn Thr Lys Lys Phe Ile Ser
                        485                 490                 495
```

-continued

```
Leu Gly Lys His Ala Lys Leu Ser Leu Gln Glu Leu Thr Trp Lys Met
            500                 505                 510

Ser Val Arg Asp Cys Ala Trp Leu Arg Arg Ser Pro Gly Val Gly Cys
        515                 520                 525

Val Pro Ala Ala Glu His Arg Leu Arg Glu Glu Ile Leu Ala Lys Phe
    530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
        595                 600                 605

His Arg Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670

Pro Gly Leu Leu Gly Ala Ser Val Leu Gly Leu Asp Asp Ile His Arg
        675                 680                 685

Ala Trp Arg Thr Phe Val Leu Arg Val Arg Ala Gln Asp Pro Pro Pro
    690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
            740                 745                 750

Gly His Val Arg Lys Ala Phe Lys Ser His Val Ser Thr Leu Thr Asp
        755                 760                 765

Leu Gln Pro Tyr Met Arg Gln Phe Val Ala His Leu Gln Glu Thr Ser
    770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
                805                 810                 815

Ala Val Arg Ile Arg Gly Lys Ser Tyr Val Gln Cys Gln Gly Ile Pro
            820                 825                 830

Gln Gly Ser Ile Leu Ser Thr Leu Leu Cys Ser Leu Cys Tyr Gly Asp
        835                 840                 845

Met Glu Asn Lys Leu Phe Ala Gly Ile Arg Arg Asp Gly Leu Leu Leu
    850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
                885                 890                 895

Val Val Asn Leu Arg Lys Thr Val Val Asn Phe Pro Val Glu Asp Glu
            900                 905                 910

Ala Leu Gly Gly Thr Ala Phe Val Gln Met Pro Ala His Gly Leu Phe
        915                 920                 925
```

```
Pro Trp Cys Gly Leu Leu Leu Asp Thr Arg Thr Leu Glu Val Gln Ser
    930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Lys Leu Phe Gly
            965                 970                 975

Val Leu Arg Leu Lys Cys His Ser Leu Phe Leu Asp Leu Gln Val Asn
            980                 985                 990

Ser Leu Gln Thr Val Cys Thr Asn Ile Tyr Lys Ile Leu Leu Leu Gln
            995                 1000                1005

Ala Tyr Arg Phe His Ala Cys Val Leu Gln Leu Pro Phe His Gln Gln
    1010                1015                1020

Val Trp Lys Asn Pro Thr Phe Phe Leu Arg Val Ile Ser Asp Thr Ala
1025                1030                1035                1040

Ser Leu Cys Tyr Ser Ile Leu Lys Ala Lys Asn Ala Gly Met Ser Leu
            1045                1050                1055

Gly Ala Lys Gly Ala Ala Gly Pro Leu Pro Ser Glu Ala Val Gln Trp
            1060                1065                1070

Leu Cys His Gln Ala Phe Leu Leu Lys Leu Thr Arg His Arg Val Thr
    1075                1080                1085

Tyr Val Pro Leu Leu Gly Ser Leu Arg Thr Ala Gln Thr Gln Leu Ser
    1090                1095                1100

Arg Lys Leu Pro Gly Thr Thr Leu Thr Ala Leu Glu Ala Ala Ala Asn
1105                1110                1115                1120

Pro Ala Leu Pro Ser Asp Phe Lys Thr Ile Leu Asp
            1125                1130

<210> SEQ ID NO 3
<211> LENGTH: 3396
<212> TYPE: DNA
<213> ORGANISM: Homo sapiens

<400> SEQUENCE: 3
atgccgcgcg ctccccgctg ccgagccgtg cgctccctgc tgcgcagcca ctaccgcgag      60
gtgctgccgc tggccacgtt cgtgcggcgc ctggggcccc agggctggcg gctggtgcag     120
cgcggggacc cggcggcttt ccgcgcgctg gtgcccagt gcctggtgtg cgtgccctgg     180
gacgcacggc cgcccccgc cgccccctcc ttccgccagg tgtcctgcct gaaggagctg     240
gtggcccgag tgctgcagag gctgtgcgag cgcggcgcga agaacgtgct ggccttcggc     300
ttcgcgctgc tggacggggc ccgcggggc ccccccgagg ccttcaccac cagcgtgcgc     360
agctacctgc ccaacacggt gaccgacgca ctgggggga gcgggcgtg ggggctgctg     420 ctgcgccgcg tgggcgacga cgtgctggtt cacctgctgg cacgctgcgc gctctttgtg     480
ctggtggctc ccagctgcgc ctaccaggtg tgcgggccgc cgctgtacca gctcggcgct     540
gccactcagg cccggccccc gccacacgct agtggacccc gaaggcgtct gggatgcgaa     600
cgggcctgga accatagcgt cagggaggcc ggggtcccc tgggcctgcc agccccgggt     660
gcgaggaggc gcgggggcag tgccagccga agtctgccgt tgcccaagag gcccaggcgt     720
ggcgctgccc ctgagccgga gcggacgccc gttgggcagg gtcctgggc ccaccccggc     780 aggacgcgtg gaccgagtga ccgtggtttc tgtgtggtgt cacctgccag accgccgaa     840 gaagccacct ctttggaggg tgcgctctct ggcacgcgcc actccacccc atccgtgggc     900
cgccagcacc acgcgggccc cccatccaca tcgcggccac cacgtccctg ggacacgcct     960
```

-continued

```
tgtcccccgg tgtacgccga gaccaagcac ttcctctact cctcaggcga caaggagcag    1020
ctgcggccct ccttcctact cagctctctg aggcccagcc tgactggcgc tcggaggctc    1080
gtggagacca tctttctggg ttccaggccc tggatgccag ggactcccg caggttgccc     1140 cgcctgcccc agcgctactg gcaaatgcgg cccctgtttc tggagctgct tgggaaccac    1200
gcgcagtgcc cctacggggt gctcctcaag acgcactgcc cgctgcgagc tgcggtcacc    1260
ccagcagccg gtgtctgtgc ccgggagaag ccccaggggc tgtggcggc ccccgaggag     1320 gaggacacag accccgtcg cctggtgcag ctgctccgcc agcacagcag ccctggcag     1380 gtgtacggct tcgtgcgggc ctgcctgcgc ggctggtgc ccccaggcct ctggggctcc     1440
aggcacaacg aacgccgctt cctcaggaac accaagaagt tcatctccct ggggaagcat    1500
gccaagctct cgctgcagga gctgacgtgg aagatgagcg tgcgggactg cgcttggctg    1560
cgcaggagcc aggggttgg ctgtgttccg gccgcagagc accgtctgcg tgaggagatc     1620
ctggccaagt cctgcactg gctgatgagt gtgtacgtcg tcgagctgct caggtctttc     1680
ttttatgtca cggagaccac gtttcaaaag aacaggctct ttttctaccg gaagagtgtc    1740
tggagcaagt tgcaaagcat tggaatcaga cagcacttga gagggtgca gctgcgggag     1800 ctgtcggaag cagaggtcag gcagcatcgg gaagccaggc ccgccctgct gacgtccaga    1860
ctccgcttca tccccaagcc tgacgggctg cggccgattg tgaacatgga ctacgtcgtg    1920
ggagccagaa cgttccgcag agaaaagagg gccgagcgtc tcacctcgag ggtgaaggca    1980
ctgttcagcg tgctcaacta cgagcgggcg cggcgcccg gcctcctggg cgcctctgtg     2040
ctgggcctgg acgatatcca cagggcctgg cgcaccttcg tgctgcgtgt gcgggcccag    2100
gacccgccgc ctgagctgta cttttgtcaag gtggatgtga cgggcgcgta cgacaccatc    2160
ccccaggaca ggctcacgga ggtcatcgcc agcatcatca acccccagaa cacgtactgc    2220
gtgcgtcggt atgccgtggt ccagaaggcc gcccatgggc acgtccgcaa ggccttcaag    2280
agccacgtct ctaccttgac agacctccag ccgtacatgc gacagttcgt ggctcacctg    2340
caggagacca gcccgctgag ggatgccgtc gtcatcgagc agagctcctc cctgaatgag    2400
gccagcagtg gcctcttcga cgtcttccta cgcttcatgt gccaccacgc cgtgcgcatc    2460
aggggcaagt cctacgtcca gtgccagggg atcccgcagg gctccatcct ctccacgctg    2520
ctctgcagcc tgtgctacgg cgacatggag aacaagctgt ttgcggggat tcggcgggac    2580
gggctgctcc tgcgtttggt ggatgatttc ttgttggtga cacctcacct cacccacgcg    2640
aaaaccttcc tcaggaccct ggtccgaggt gtccctgagt atggctgcgt ggtgaacttg    2700
cggaagacag tggtgaactt ccctgtagaa gacgaggccc tgggtggcac ggcttttgtt    2760
cagatgccgg cccacggcct attccctgg tgcggcctgc tgctggatac ccggaccctg    2820
gaggtgcaga gcgactactc cagctatgcc cggacctcca tcagagccag tctcaccttc    2880
aaccgcggct tcaaggctgg gaggaacatg cgtcgcaaac tctttgggt cttgcggctg    2940 aagtgtcaca gcctgtttct ggatttgcag gtgaacagcc tccagacggt gtgcaccaac    3000
atctacaaga tcctcctgct gcaggcgtac aggtttcacg catgtgtgct gcagctccca    3060
tttcatcagc aagtttggaa gaaccccaca tttttcctgc gcgtcatctc tgacacggcc    3120
tccctctgct actccatcct gaaagccaag aacgcaggga tgtcgctggg gccaagggc     3180 gccgccggcc ctctgcccct cgaggccgtg cagtggctgt gccaccaagc attcctgctc    3240
aagctgactc gacaccgtgt cacctacgt ccactcctgg ggtcactcag acagcccag      3300 acgcagctga gtcggaagct cccggggacg acgctgactg ccctggaggc cgcagccaac    3360
```
ccggcactgc cctcagactt caagaccatc ctggac 3396

<210> SEQ ID NO 4
<211> LENGTH: 1132
<212> TYPE: PRT
<213> ORGANISM: Homo sapiens
<400> SEQUENCE: 4

```
Met Pro Arg Ala Pro Arg Cys Arg Ala Val Arg Ser Leu Leu Arg Ser
 1               5                  10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
```

```
              370                 375                 380
Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
                420                 425                 430

Gly Ser Val Ala Ala Pro Glu Glu Asp Thr Asp Pro Arg Arg Leu
                435                 440                 445

Val Gln Leu Leu Arg Gln His Ser Ser Pro Trp Gln Val Tyr Gly Phe
    450                 455                 460

Val Arg Ala Cys Leu Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
                500                 505                 510

Ser Val Arg Asp Cys Ala Trp Leu Arg Arg Ser Pro Gly Val Gly Cys
                515                 520                 525

Val Pro Ala Ala Glu His Arg Leu Arg Glu Glu Ile Leu Ala Lys Phe
530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
                580                 585                 590

Leu Lys Arg Val Gln Leu Arg Glu Leu Ser Glu Ala Glu Val Arg Gln
    595                 600                 605

His Arg Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
                660                 665                 670

Pro Gly Leu Leu Gly Ala Ser Val Leu Gly Leu Asp Asp Ile His Arg
                675                 680                 685

Ala Trp Arg Thr Phe Val Leu Arg Val Arg Ala Gln Asp Pro Pro Pro
    690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
                740                 745                 750

Gly His Val Arg Lys Ala Phe Lys Ser His Val Ser Thr Leu Thr Asp
                755                 760                 765

Leu Gln Pro Tyr Met Arg Gln Phe Val Ala His Leu Gln Glu Thr Ser
    770                 775                 780

Pro Leu Arg Asp Ala Val Val Ile Glu Gln Ser Ser Ser Leu Asn Glu
785                 790                 795                 800
```

```
Ala Ser Ser Gly Leu Phe Asp Val Phe Leu Arg Phe Met Cys His His
                805                 810                 815
Ala Val Arg Ile Arg Gly Lys Ser Tyr Val Gln Cys Gln Gly Ile Pro
            820                 825                 830
Gln Gly Ser Ile Leu Ser Thr Leu Leu Cys Ser Leu Cys Tyr Gly Asp
        835                 840                 845
Met Glu Asn Lys Leu Phe Ala Gly Ile Arg Arg Asp Gly Leu Leu Leu
    850                 855                 860
Arg Leu Val Asp Asp Phe Leu Leu Val Thr Pro His Leu Thr His Ala
865                 870                 875                 880
Lys Thr Phe Leu Arg Thr Leu Val Arg Gly Val Pro Glu Tyr Gly Cys
                885                 890                 895
Val Val Asn Leu Arg Lys Thr Val Val Asn Phe Pro Val Glu Asp Glu
            900                 905                 910
Ala Leu Gly Gly Thr Ala Phe Val Gln Met Pro Ala His Gly Leu Phe
        915                 920                 925
Pro Trp Cys Gly Leu Leu Leu Asp Thr Arg Thr Leu Glu Val Gln Ser
    930                 935                 940
Asp Tyr Ser Ser Tyr Ala Arg Thr Ser Ile Arg Ala Ser Leu Thr Phe
945                 950                 955                 960
Asn Arg Gly Phe Lys Ala Gly Arg Asn Met Arg Arg Lys Leu Phe Gly
                965                 970                 975
Val Leu Arg Leu Lys Cys His Ser Leu Phe Leu Asp Leu Gln Val Asn
            980                 985                 990
Ser Leu Gln Thr Val Cys Thr Asn Ile Tyr Lys Ile Leu Leu Leu Gln
        995                 1000                1005
Ala Tyr Arg Phe His Ala Cys Val Leu Gln Leu Pro Phe His Gln Gln
    1010                1015                1020
Val Trp Lys Asn Pro Thr Phe Phe Leu Arg Val Ile Ser Asp Thr Ala
1025                1030                1035                1040
Ser Leu Cys Tyr Ser Ile Leu Lys Ala Lys Asn Ala Gly Met Ser Leu
                1045                1050                1055
Gly Ala Lys Gly Ala Gly Pro Leu Pro Ser Glu Ala Val Gln Trp
            1060                1065                1070
Leu Cys His Gln Ala Phe Leu Leu Lys Leu Thr Arg His Arg Val Thr
        1075                1080                1085
Tyr Val Pro Leu Leu Gly Ser Leu Arg Thr Ala Gln Thr Gln Leu Ser
    1090                1095                1100
Arg Lys Leu Pro Gly Thr Thr Leu Thr Ala Leu Glu Ala Ala Ala Asn
1105                1110                1115                1120
Pro Ala Leu Pro Ser Asp Phe Lys Thr Ile Leu Asp
                1125                1130

<210> SEQ ID NO 5
<211> LENGTH: 20
<212> TYPE: PRT
<213> ORGANISM: Homo sapiens

<400> SEQUENCE: 5

Met Pro Arg Ala Pro Arg Cys Arg Ala Val Arg Ser Leu Leu Arg Ser
1               5                   10                  15

His Tyr Arg Glu
            20

<210> SEQ ID NO 6
<211> LENGTH: 20
```

```
-continued

<212> TYPE: PRT
<213> ORGANISM: Homo sapiens

<400> SEQUENCE: 6

Met Pro Arg Ala Pro Arg Cys Arg Ala Val Arg Ser Leu Leu Arg Ala
 1               5                  10                  15

His Tyr Arg Glu
            20
```

NUCLEAR TELOMERASE REVERSE TRANSCRIPTASE VARIANT

CROSS REFERENCE TO RELATED APPLICATION

This application claims priority under 35 USC §119(e) from U.S. Provisional Application Ser. No. 61/132,673, filed Jun. 19, 2008, which application is herein specifically incorporated by reference in its entirety.

FIELD OF THE INVENTION

The present invention relates to novel telomerase genes and proteins. In particular, the present invention is directed to a novel variant of human telomerase reverse transcriptase, which displays properties distinct from those of wildtype telomerase reverse transcriptase and methods of use thereof.

BACKGROUND OF THE INVENTION

Several publications and patent documents are referenced in this application in order to more fully describe the state of the art to which this invention pertains. The disclosure of each of these publications and documents is incorporated by reference herein.

Telomeres, the protein-DNA structures physically located on the ends of the eukaryotic organisms, are required for chromosome stability and are involved in chromosomal organization within the nucleus (See e.g., Zakian, Science 270: 1601 [1995]; Blackburn and Gall, J. Mol. Biol., 120:33 [1978]; Oka et al., Gene 10:301 [1980]; and Klobutcher et al., Proc. Natl. Acad. Sci., 78:3015 [1981]). Telomeres are believed to be essential in such organisms as yeast and probably most other eukaryotes, as they allow cells to distinguish intact from broken chromosomes, protect chromosomes from degradation, and act as substrates for novel replication mechanisms. Telomeres are generally replicated in a complex, cell cycle and developmentally regulated manner by telomerase, a telomere-specific DNA polymerase. Telomerase-independent means for telomere maintenance have, however, been described. In that telomere loss is associated with chromosomal changes such as those that occur in cancer and aging, the study of telomeres and mechanisms contributing to their regulation have been at the center of intense investigations.

Telomeric DNA: In most organisms, telomeric DNA has been reported to consist of a tandem array of very simple sequences, which in many cases are short and precise. Typically, telomeres consist of simple repetitive sequences rich in G residues in the strand that runs 5' to 3' toward the chromosomal end. Heterogeneous telomeric sequences have, however, been reported in some organisms. In addition, the repeated telomeric sequence in some organisms is much longer. The telomeric DNA sequences of many organisms have been determined (See e.g., Zakian, Science 270:1601 [1995]) and such studies have revealed that only limited consensus exists among these sequences (Zakian, supra). The average amount of telomeric DNA also varies among organisms. Moreover, in most organisms, the amount of telomeric DNA fluctuates. Heterogeneity and spontaneous changes in telomere length are thought to reflect a complex balance between the processes involved in degradation and lengthening of telomeric tracts. In addition, other factors including genetic and nutritional influences may cause increases or decreases in telomeric length (Lustig and Petes, Natl. Acad. Sci., 83:1398 [1986]; and Sandell et al., Cell 91:12061 [1994]). The inherent heterogeneity of virtually all telomeric DNAs suggests that telomeres are not maintained via conventional replicative processes.

Telomere Replication: Complete replication of the ends of linear eukaryotic chromosomes presents special problems for conventional methods of DNA replication. For example, conventional DNA polymerases cannot begin DNA synthesis de novo, rather, they require RNA primers which are later removed during replication. In the case of telomeres, removal of the RNA primer from the lagging-strand end would necessarily leave a 5'-terminal gap, resulting in the loss of sequence if the parental telomere was blunt-ended (Watson, Nature New Biol., 239:197 [1972]; Olovnikov, J. Theor. Biol., 41:181 [1973]). However, the described telomeres have 3' overhangs (Klobutcher et al., Proc. Natl. Acad. Sci., 58:3015 [1981]; Henderson and Blackburn, Mol. Cell. Biol., 9:345 [1989]; and Wellinger et al., Cell 72:51 [1993]). For these molecules, it is possible that removal of the lagging-strand 5'-terminal RNA primer could regenerate the 3' overhang without loss of sequence on this side of the molecule. Loss of sequence information on the leading-strand end would, however, occur due to the lack of a complementary strand to act as template in the synthesis of a 3' overhang (Zahler and Prescott, Nucleic Acids Res., 16:6953 [1988]; Lingner et al., Science 269:1533 [1995]).

While conventional DNA polymerases cannot accurately reproduce chromosomal DNA ends, specialized factors exist to ensure their complete replication. Telomerase (TERT) is a key component in this process. Telomerase is a ribonucleoprotein (RNP) particle and polymerase that uses a portion of its internal RNA moiety as a template for telomere repeat DNA synthesis (Yu et al., Nature 344:126 [1990]; Singer and Gottschling, Science 266:404 [1994]; Autexier and Greider, Genes Develop., 8:563 [1989]; Gilley et al., Genes Develop., 9:2214 [1995]; McEachern and Blackburn, Nature 367:403 [1995]; Blackburn, Ann. Rev. Biochem., 61:113 [1992];. Greider, Ann. Rev. Biochem., 65:337 [1996]). The activity of this enzyme depends upon both its RNA and protein components to circumvent the problems presented by end replication by using RNA (i.e., as opposed to DNA) to template the synthesis of telomeric DNA. Telomerases extend the G strand of telomeric DNA. A combination of factors, including telomerase processivity, frequency of action at individual telomeres, and the rate of degradation of telomeric DNA, contribute to the size of the telomeres (i.e., whether they are lengthened, shortened, or maintained at a certain size).

Notably, telomere replication is regulated both by developmental and cell cycle factors. It has been hypothesized that aspects of telomere replication may act as signals in the cell cycle. For example, certain DNA structures or DNA-protein complex formations may act as a checkpoint to indicate that chromosomal replication has been completed (See e.g., Wellinger et al., Mol. Cell. Biol., 13:4057 [1993]). In addition, it has been observed that in humans, telomerase activity is not detectable in most somatic tissues, although it is detected in many tumors (Wellinger, supra). Thus, telomere length may serve as a mitotic clock, which serves to limit the replication potential of cells in vivo and/or in vitro. In light of the contribution of telomerase to maintenance of telomere function and activity, telomerase is a bona fide target for development of agents directed to cancer therapy and/or slowing of aging processes.

SUMMARY OF THE INVENTION

Like other telomerases, human telomerase is composed minimally of two different subunits, a catalytic core (hTERT)

and an RNA component (hTR). Together, they work in concert to replenish telomeres with every cell division. The present invention is directed to the discovery of a novel mutant of hTERT that exhibits altered cellular localization and functional activity with respect to wildtype hTERT.

In one aspect of the invention, the present inventor has generated a novel mutant of hTERT (S16AhTERT) that is exclusively targeted to the nucleus. Expression of S16AhTERT renders cells resistant to both mtDNA damage as well as apoptosis induced by $H_2O_2$. These findings demonstrate that forced expression of telomerase to the nucleus is a useful therapeutic strategy for making cells more resistant to oxidative damage and apoptotic death. Moreover, expression of telomerase only in the nucleus is particularly useful in situations where telomere elongation is required without the associated effects of hTERT in the mitochondria.

Applications for which expression of S16AhTERT polypeptide is therapeutically useful, therefore, include treatment of degenerative diseases that are characterized by the loss of cells (such as neurons), diseases that relate to telomere shortening such as macular degeneration, arteriosclerosis, cirrhosis of the liver, kidney disease, diabetes, Alzheimer's Disease, Parkinson's Disease, osteoporosis and disorders that have an inflammatory component. With respect to disorders that have an inflammatory component, expression of S16AhTERT would be particularly useful in situations wherein oxidative stress caused by inflammation is damaging the cells without killing them. Use of the mutant would render cells more resistant to oxidative damage. Moreover, rare genetic disorders that are believed to originate from defective telomere building, such as progeria or dyskeratosis, would also benefit from therapy with this mutant.

The present invention can also be used to ameliorate signs of the normal process of aging. Cosmetic use of the telomerase mutant for regenerating skin and reducing wrinkles is also envisioned. There is also evidence that hTERT can be used to stimulate native stem cells, cause hair regrowth, and reverse graying. Improvements in cell culture technology that stem from expression of S16AhTERT may also be used to extend the lifespan of mammalian cell cultures, without the negative effect of telomerase in mitochondria. Such an approach would enhance cell growth and thus, enable longer screening assays such as those performed with respect to pharmaceutical products or similar studies. The expression of S16AhTERT can also be used to enhance ex vivo growth of skin and other organs intended for grafting and/or transplantation. Indeed, telomere exhaustion is known to be a problem when growing skin and organs in a lab and the hTERT mutant described herein could be used to address this problem without introducing side effects associated with mitochondrial expression. Expression of S16AhTERT may also prove useful for increasing the life or healthspan of an organism.

Accordingly, the present invention is directed to an isolated nucleic acid sequence encoding a polypeptide comprising SEQ ID NO: 2 (S16AhTERT), or a functional fragment thereof, wherein said polypeptide exhibits an activity of S16AhTERT, for example, is targeted for nuclear expression and is capable of rendering cells more resistant to oxidative damage and apoptotic death. In accordance with the present invention, expression of a polypeptide comprising SEQ ID NO: 2 (S16AhTERT), or a functional fragment thereof, renders cells in which it is expressed more resistant to oxidative damage and apoptotic death relative to control cells which do not express the polypeptide comprising SEQ ID NO: 2 (S16AhTERT). Also included are expression vectors comprising an isolated nucleic acid sequence which encodes an amino acid sequence of the invention (e.g., SEQ ID NO: 2), wherein expression of the nucleic acid sequence is controlled by regulatory sequences in an expression vector. Cells comprising such expression vectors are also encompassed. In yet another aspect, a transgenic animal comprising an isolated nucleic acid sequence encoding a polypeptide comprising SEQ ID NO: 2, wherein the polypeptide is S16AhTERT polypeptide or functional fragment thereof, capable of exhibiting a S16AhTERT activity, and the nucleic acid sequence is expressed in at least one cell of the transgenic animal.

In another aspect of the invention, an isolated amino acid sequence comprising a polypeptide of SEQ ID NO: 2, or a functional fragment thereof, wherein said polypeptide is capable of exhibiting a S16AhTERT activity, is presented. As described herein, S16AhTERT activities include the ability to render cells more resistant to oxidative damage and apoptotic death, and to elongate telomeres (thus immortalizing cells). In accordance with the present invention, expression of a polypeptide comprising SEQ ID NO: 2 (S16AhTERT), or a functional fragment thereof, renders cells in which it is expressed more resistant to oxidative damage and apoptotic death and promotes telomere elongation in cells in which it is expressed, as determined relative to control cells which do not express the polypeptide comprising SEQ ID NO: 2 (S16AhTERT). Also included are expression vectors encoding an amino acid sequence of the invention (e.g., SEQ ID NO: 2), wherein expression of the amino acid sequence is controlled by regulatory sequences in the expression vector, cells comprising such expression vectors, and transgenic animals comprising an amino acid sequence of the invention, wherein the amino acid sequence is expressed in at least one cell in the transgenic animal.

In another aspect of the invention, an isolated nucleic acid sequence comprising SEQ ID NO: 1 is provided, wherein the nucleic acid sequence encodes S16AhTERT or a functional fragment thereof capable of exhibiting an activity attributable to S16AhTERT as described herein. Also described is an expression vector comprising a nucleic acid sequence of SEQ ID NO: 1, wherein the nucleic acid sequence encodes S16AhTERT or a functional fragment thereof capable of exhibiting an S16AhTERT activity, and SEQ ID NO: 1 is operably linked to a regulatory sequence. Moreover, a cell comprising such an expression vector is also within the scope of the invention. In another aspect, a transgenic animal or plant comprising a nucleic acid sequence comprising SEQ ID NO: 1, wherein the nucleic acid sequence encodes S16AhTERT or a functional fragment thereof capable of exhibiting an S16AhTERT activity, and wherein the nucleic acid sequence is expressed in at least one cell of the transgenic animal/plant is presented.

The present invention also encompasses an antibody immunologically specific for an amino acid sequence comprising SEQ ID NO: 2. Such antibodies can be polyclonal or monoclonal antibodies and functional fragments thereof.

The present invention encompasses a method for promoting cellular resistance to oxidative damage and apoptotic death and telomere extension in the absence of mitochondrial sensitization, the method comprising expressing a polypeptide comprising SEQ ID NO: 2 in a cell, wherein expression of the polypeptide promotes cellular resistance to oxidative damage and apoptotic death and telomere extension in the absence of mitochondrial sensitization in the cell relative to a control cell wherein said polypeptide is not expressed. In a particular embodiment, the cell in which a polypeptide comprising SEQ ID NO: 2 is expressed is in vitro. In a different embodiment, the cell in which a polypeptide comprising SEQ ID NO: 2 is expressed is in vivo.

The present invention also includes a kit comprising an isolated nucleic acid sequence comprising SEQ ID NO: 1, wherein the nucleic acid sequence encodes a S16AhTERT polypeptide or functional fragment thereof; an isolated nucleic acid sequence encoding an amino acid sequence comprising SEQ ID NO: 2 or a functional fragment thereof; an isolated amino acid sequence comprising SEQ ID NO: 2, wherein the amino acid sequence is an S16AhTERT polypeptide or functional fragment thereof; a S16AhTERT activity compatible buffer; at least one antibody immunologically specific for S16AhTERT; and instructional materials.

Also described is a composition comprising at least one S16AhTERT polypeptide or functional fragment thereof, S16AhTERT encoding nucleic acid sequence, and at least one antibody immunologically specific for S16AhTERT identified using the methods of the invention and a pharmaceutically acceptable buffer.

Compositions containing the molecules or compounds of the invention can be administered for therapeutic purposes. In therapeutic applications, compositions comprising S16AhTERT or a functional fragment or derivative thereof are administered to a patient suffering from a degenerative disease associated with telomere shortening, apoptosis, or inflammatory disorder (such as, e.g., Alzheimer's disease, macular degeneration, cardiomyopathy or arthritis) in an amount sufficient to cure or at least partially arrest or ameliorate the symptoms of the disease and its complications. An amount adequate to accomplish this is defined as a "therapeutically effective amount or dose". Compositions comprising a nucleic acid encoding the S16AhTERT polypeptide or a functional fragment or derivative thereof may also be used to deliver a therapeutically effective amount or dose of S16AhTERT or a functional fragment or derivative thereof to a patient in need thereof. Expression vectors comprising a nucleic acid encoding the S16AhTERT polypeptide or a functional fragment or derivative thereof are of utility for such therapeutic applications. Amounts effective for this use will depend on the severity of the disease and the weight and general state of the patient.

Compositions comprising S16AhTERT or a functional fragment or derivative thereof may also be administered to a patient to delay or reduce normal processes associated with aging.

In an aspect of the invention, a method for treating a subject with a degenerative disorder is presented comprising administering to the subject a therapeutically effective amount of SEQ ID NO: 2 or a functional fragment or derivative thereof, wherein said administering achieves delivery of SEQ ID NO: 2 or a functional fragment or derivative thereof to degenerative/dysfunctional cells that lose normal function over time in the subject, and said delivery renders the degenerative/dysfunctional cells more resistant to oxidative damage and apoptotic death, while allowing telomere elongation.

In another aspect of the invention, a method for treating a subject with (i) disorders characterized by telomere shortening/dysfunction; (ii) disorders characterized by neurodegeneration; (iii) disorders caused by uncontrolled inflammation; (v) disorders related to chronic infection and oxidative stress (such as hepatitis) and (v) normal aging processes is presented comprising administering to the subject a therapeutically effective amount of SEQ ID NO: 2 or a functional fragment or derivative thereof, wherein said administering achieves delivery of SEQ ID NO: 2 or a functional fragment or derivative thereof to cells that lose normal function over time in the subject, and said delivery renders the cells more resistant to oxidative damage and apoptotic death, while allowing telomere elongation.

Accordingly, the invention encompasses a method of treating a subject with a degenerative disorder, the method comprising administering to the subject a therapeutically effective amount of SEQ ID NO: 2 or a functional fragment or derivative thereof, wherein the administering achieves delivery of SEQ ID NO: 2 or a functional fragment or derivative thereof to degenerative/dysfunctional cells in the subject, and the delivery renders the degenerative cells more resistant to oxidative damage and apoptotic death. In certain embodiments, the method may further comprise a second therapeutic agent used to treat the degenerative disorder. Second therapeutic agents that are used in combination with a therapeutically effective amount of SEQ ID NO: 2 or a functional fragment or derivative thereof to treat a degenerative disorder in accordance with the present invention, include those used to treat neurodegenerative disorders, inflammatory disorders, and cardiomyopathy. Such therapeutic agents are known to skilled practitioners.

In certain embodiments of the invention, the degenerative disorder is a neurodegenerative disorder. Such neurodegenerative disorders include, for example: Alzheimer's disease, Parkinson's disease, ALS, multiple sclerosis, ataxias (e.g., Friedereich Ataxia) and Huntington's Disease.

In another embodiment of the invention, the degenerative disorder is an inflammatory disorder. Such inflammatory disorders include, for example: arthritis, atherosclerosis, pelvic inflammatory disease (PID), Inflammatory Bowel Disease (IBD) ulcerative colitis (UC), Lung inflammatory disease, breast inflammation, inflammatory diseases of the intestine, rheumatoid arthritis (RA), Crohn's disease, tuberculosis inflammatory breast cancer, inflammatory skin disease, and psoriasis.

Other features and advantages of the invention will be apparent from the following description of the preferred embodiments thereof, and from the claims.

DETAILED DESCRIPTION OF THE INVENTION

Figure 1:
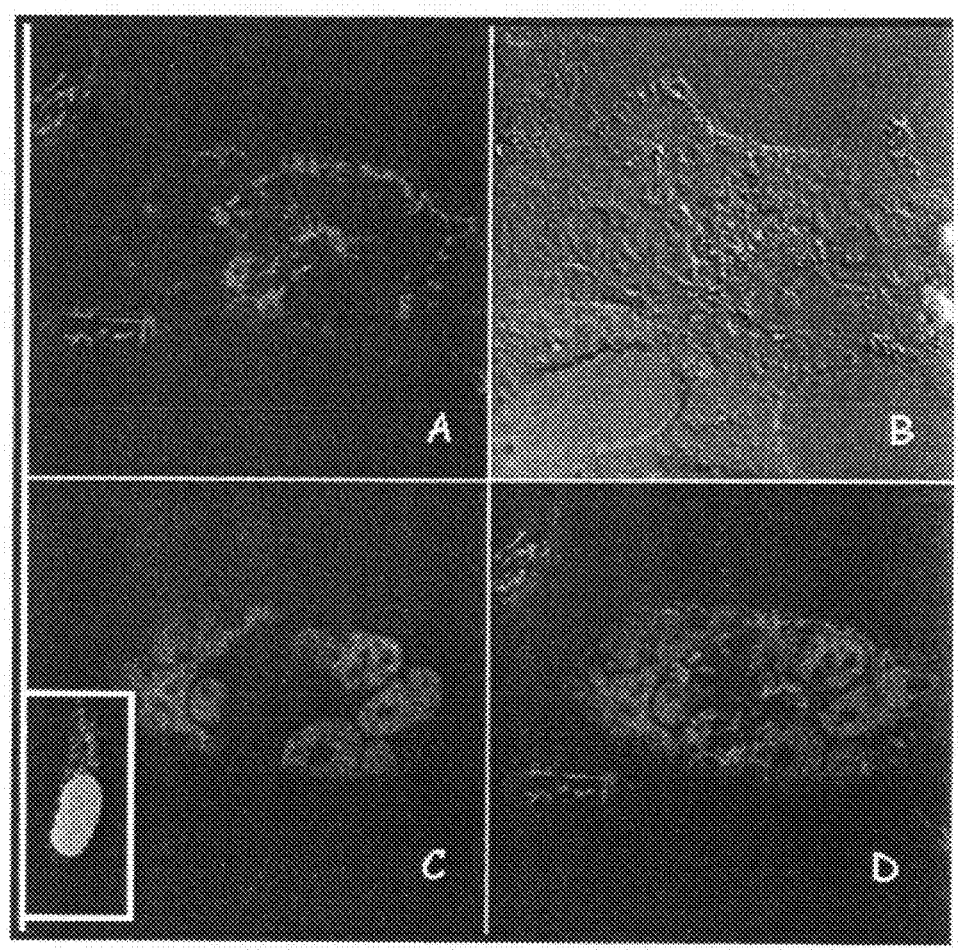
FIG. 1A-D. S16AhTERT-EGFP localizes only to the nucleus. Top, N-terminal sequence of hTERT (bold: amino acids of the MLS); the respective amino acid substitutions are underlined. Mitochondria alone (A); WT hTERT-EGFP fusion protein (inset) and S16AhTERT-EGFP (C); (D) merge of images A and C. (B) Phase contrast image. Red: Mitotracker, green: EGFP, yellow: merge of both images.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

As noted above, the terms used herein have the meanings recognized and known to those of skill in the art. However, for convenience and completeness, particular terms and their meanings are set forth below.

In order to more clearly set forth the parameters of the present invention, the following definitions are used:

As used in this specification and the appended claims, the singular forms "a", "an", and "the" include plural references unless the context clearly dictates otherwise. Thus for example, reference to "the method" includes one or more methods, and/or steps of the type described herein and/or which will become apparent to those persons skilled in the art upon reading this disclosure.

The term "complementary" refers to two DNA strands that exhibit substantial normal base pairing characteristics. Complementary DNA may, however, contain one or more mismatches.

The term "hybridization" refers to the hydrogen bonding that occurs between two complementary DNA strands.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it is generally associated in its natural state (i.e., in cells or tissues). An isolated nucleic acid (either DNA or RNA) may further represent a molecule produced directly by biological or synthetic means and separated from other components present during its production.

"Natural allelic variants", "mutants" and "derivatives" of particular sequences of nucleic acids refer to nucleic acid sequences that are closely related to a particular sequence but which may possess, either naturally or by design, changes in sequence or structure. By closely related, it is meant that at least about 60%, but often, more than 85%, of the nucleotides of the sequence match over the defined length of the nucleic acid sequence referred to using a specific SEQ ID NO. Changes or differences in nucleotide sequence between closely related nucleic acid sequences may represent nucleotide changes in the sequence that arise during the course of normal replication or duplication in nature of the particular nucleic acid sequence. Other changes may be specifically designed and introduced into the sequence for specific purposes, such as to change an amino acid codon or sequence in a regulatory region of the nucleic acid. Such specific changes may be made in vitro using a variety of mutagenesis techniques or produced in a host organism placed under particular selection conditions that induce or select for the changes. Such sequence variants generated specifically may be referred to as "mutants" or "derivatives" of the original sequence.

The terms "percent similarity", "percent identity" and "percent homology" when referring to a particular sequence are used as set forth in the University of Wisconsin GCG software program and are known in the art.

The present invention also includes active portions, fragments, derivatives and functional or non-functional mimetics of a mutant hTERT polypeptide or protein of the invention. An "active portion" of a mutant hTERT polypeptide refers to a peptide that is less than the full length mutant hTERT polypeptide, but which retains measurable biological activity.

A "fragment" or "portion" of a mutant hTERT polypeptide means a stretch of amino acid residues of at least about five to seven contiguous amino acids, often at least about seven to nine contiguous amino acids, typically at least about nine to thirteen contiguous amino acids and, most preferably, at least about twenty to thirty or more contiguous amino acids. A "derivative" of the mutant hTERT polypeptide or a fragment thereof means a polypeptide modified by varying the amino acid sequence of the protein, e.g. by manipulation of the nucleic acid encoding the protein or by altering the protein itself. Such derivatives of the natural amino acid sequence may involve insertion, addition, deletion or substitution of one or more amino acids, and may or may not alter the essential activity of the original mutant hTERT polypeptide.

Different "variants" of the mutant hTERT polypeptide may be generated. The skilled person can produce variants having single or multiple amino acid substitutions, deletions, additions or replacements. These variants may include inter alia: (a) variants in which one or more amino acids residues are substituted with conservative or non-conservative amino acids, (b) variants in which one or more amino acids are added to the mutant hTERT polypeptide, (c) variants in which one or more amino acids include a substituent group, and (d) variants in which the mutant hTERT polypeptide is fused with another peptide or polypeptide such as a fusion partner, a protein tag or other chemical moiety, that may confer useful properties to the mutant hTERT polypeptide, such as, for example, an epitope for an antibody, a polyhistidine sequence, a biotin moiety and the like. Other mutant hTERT polypeptides of the invention include variants in which amino acid residues from one species are substituted for the corresponding residue in another species, either at conserved or non-conserved positions. In another embodiment, amino acid residues at non-conserved positions are substituted with conservative or non-conservative residues. The techniques for obtaining these variants, including genetic (suppressions, deletions, mutations, etc.), chemical, and enzymatic techniques are known to a person having ordinary skill in the art.

To the extent such analogues, fragments, derivatives, mutants, and modifications, including alternative nucleic acid processing forms and alternative post-translational modification forms result in derivatives of a mutant hTERT polypeptide that retain any of the biological properties characteristic of the mutant hTERT polypeptide, they are included within the scope of this invention.

The term "functional" as used herein implies that the nucleic or amino acid sequence is functional for the recited assay or purpose.

The term "functional fragment" as used herein implies that the nucleic or amino acid sequence is a portion or subdomain of a full length polypeptide and is functional for the recited assay or purpose.

The phrase "consisting essentially of" when referring to a particular nucleotide or amino acid means a sequence having the properties of a given SEQ ID NO:. For example, when used in reference to an amino acid sequence, the phrase includes the sequence per se and molecular modifications that would not affect the basic and novel characteristics of the sequence.

A "replicon" is any genetic element, for example, a plasmid, cosmid, bacmid, phage or virus that is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element.

An "expression vector" or "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

As used herein, the term "operably linked" refers to a regulatory sequence capable of mediating the expression of a coding sequence and which are placed in a DNA molecule (e.g., an expression vector) in an appropriate position relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

As used herein, the terms "nucleic acid", "polynucleotide" and "oligonucleotide" refer to primers, probes, and oligomer fragments to be detected, and shall be generic to polydeoxyribonucleotides (containing 2-deoxy-D-ribose), to polyribonucleotides (containing D-ribose), and to any other type of polynucleotide which is an N-glycoside of a purine or pyrimidine base, or modified purine or pyrimidine bases (including abasic sites). There is no intended distinction in length between the term "nucleic acid", "polynucleotide" and "oligonucleotide", and these terms will be used interchangeably. These terms refer only to the primary structure of the molecule. Thus, these terms include double- and single-stranded DNA, as well as double- and single-stranded RNA.

The term "oligonucleotide," as used herein refers to primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

RNA interference (RNAi) is an evolutionarily conserved mechanism in plant and animal cells that directs the degradation of messenger RNAs homologous to short double-stranded RNAs termed "small interfering RNA" or "siRNA" or "short hairpin RNA" or "shRNA". The ability of siRNA to direct gene silencing in mammalian cells has raised the possibility that siRNA might be used to investigate gene function in a high throughput fashion or to modulate gene expression in human diseases. Methods of preparing siRNAs are known to those skilled in the art. The following references are incorporated herein by reference in their entirety: Reich et al., *Mol Vis.* 9:210-6 (2003); Gonzalez-Alegre P et al., *Ann Neurol.* 53:781-7 (2003); Miller et al., *Proc Natl Acad Sci USA.* (2003); Bidere et al., *J Biol Chem.*, published as manuscript M301911200 (Jun. 2, 2003); Van De Wetering et al., EMBO Rep. 4:609-15 (2003); Miller and Grollman, *DNA Repair (Amst)* 2:759-63 (2003); Kawakami et al., *Nat Cell Biol.* 5:513-9 (2003); Abdelrahim et al., *Mol Pharmacol.* 63:1373-81 (2003); Williams et al., *J Immunol.* 170:5354-8 (2003); Daude et al., *J Cell Sci.* 116:2775-9 (2003); Jackson et al., *Nat Biotechnol.* 21:635-7 (2003); Dillin, *Proc Natl Acad Sci USA.* 100:6289-91 (2003); Matta et al., *Cancer Biol Ther.* 2:206-10 (2003); Wohlbold et al., *Blood.* (2003); Julien and Herr, *EMBO J* 22:2360-9 (2003); Scherr et al., *Cell Cycle.* 2:251-7 (2003); Giri et al., *J Immunol.* 170:5281-94 (2003); Liu and Erikson, *Proc Natl Acad Sci USA.* 100:5789-94 (2003); Chi et al., *Proc Natl Acad Sci USA.* 100:6343-6 (2003); Hall and Alexander, *J Virol.* 77:6066-9 (2003).

"Antisense" nucleic acids are DNA or RNA molecules that are complementary to at least a portion of a specific mRNA molecule (See Weintraub, *Sci. Amer.* 262:40-46 (1990); Marcus-Sekura, *Nucl. Acid Res,* 15: 5749-5763 (1987); Marcus-Sekura *Anal Biochem.,* 172:289-295 (1988); Brysch et al., *Cell Mol. Neurobiol.,* 14:557-568 (1994)). In the cell, the single stranded antisense molecule hybridizes to that mRNA, forming a double stranded molecule. The cell does not translate an mRNA in this double-stranded form. Therefore, antisense nucleic acids interfere with the expression of mRNA into protein. Oligomers of greater than about fifteen nucleotides and molecules that hybridize to the AUG initiation codon will be particularly efficient. Antisense methods have been used to inhibit the expression of many genes in vitro (Marcus-Sekura, *Anal. Biochem.,* 172:289-295 (1988); Hambor et al., *Proc. Natl. Acad. Sci. USA.* 85:4010-4014 (1988)) and in situ (Arima et al., *Antisense Nucl. Acid Drug Dev.* 8:319-327 (1998); Hou et al., *Antisense Nuc. Acid Drug Dev.* 8:295-308 (1998)).

Splicing variants of hTERT, for example, that exhibit differential cellular localization (e.g., nuclear or mitochondrial) and are, therefore, physically separated at the RNA level can be targeted differentially using techniques such as those described above with respect to siRNA.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Primers may be labeled fluorescently with 6-carboxyfluorescein (6-FAM). Alternatively primers may be labeled with 4,7,2',7'-Tetrachloro-6-carboxyfluorescein (TET). Other alternative DNA labeling methods are known in the art and are contemplated to be within the scope of the invention.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

The term "substantially pure" refers to a preparation comprising at least 50-60% by weight of a given material (e.g., nucleic acid, oligonucleotide, protein, etc.). More preferably, the preparation comprises at least 75% by weight, and most preferably 90-95% by weight of the given compound. Purity is measured by methods appropriate for the given compound (e.g. chromatographic methods, agarose or polyacrylamide gel electrophoresis, HPLC analysis, and the like). "Mature protein" or "mature polypeptide" shall mean a polypeptide possessing the sequence of the polypeptide after any processing events that normally occur to the polypeptide during the course of its genesis, such as proteolytic processing from a polypeptide precursor. In designating the sequence or boundaries of a mature protein, the first amino acid of the mature protein sequence is designated as amino acid residue 1.

The term "tag", "tag sequence" or "protein tag" refers to a chemical moiety, either a nucleotide, oligonucleotide, polynucleotide or an amino acid, peptide or protein or other chemical, that when added to another sequence, provides additional utility or confers useful properties to the sequence, particularly with regard to methods relating to the detection or isolation of the sequence. Thus, for example, a homopolymer nucleic acid sequence or a nucleic acid sequence complementary to a capture oligonucleotide may be added to a primer or probe sequence to facilitate the subsequent isolation of an extension product or hybridized product. In the case of protein tags, histidine residues (e.g., 4 to 8 consecutive histidine residues) may be added to either the amino- or carboxy-terminus of a protein to facilitate protein isolation by chelating metal chromatography. Alternatively, amino acid sequences, peptides, proteins or fusion partners representing epitopes or binding determinants reactive with specific antibody molecules or other molecules (e.g., flag epitope, c-myc epitope, transmembrane epitope of the influenza A virus hemaglutinin protein, protein A, cellulose binding domain, calmodulin binding protein, maltose binding protein, chitin binding domain, glutathione S-transferase, and the like) may be added to proteins to facilitate protein isolation by procedures such as affinity or immunoaffinity chromatography. Chemical tag moieties include such molecules as biotin, which may be added to either nucleic acids or proteins and facilitate isolation or detection by interaction with avidin reagents, and the like. Numerous other tag moieties are known to, and can be envisioned by, the trained artisan, and are contemplated to be within the scope of this definition.

The terms "transform", "transfect", "transduce", "infect", shall refer to any method or means by which a nucleic acid is introduced into a cell or host organism and may be used interchangeably to convey the same meaning. Such methods include, but are not limited to, transfection, electroporation, microinjection, PEG-fusion and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. In other applications, the introduced nucleic acid may exist in the recipient cell or host organism only transiently.

A "clone" or "clonal cell population" is a population of cells derived from a single cell or common ancestor by mitosis.

A "cell line" is a clone of a primary cell or cell population that is capable of stable growth in vitro for many generations.

As used herein, the term "degenerative disease" or "degenerative disorder" refers to a disease in which the function or structure of the affected tissues or organs progressively deteriorates over time, whether due to normal bodily wear, lifestyle choices such as exercise or eating habits, environmental exposure (such as with pesticides) or due to infection (such as hepatitis).

As used herein, the term "neurodegenerative disease" or "neurodegenerative disorder" refers to diseases that result from deterioration of neurons which over time will lead to neurodegeneration and disabilities resulting from neuronal loss. They are divided into two groups according to phenotypic effects, which are not mutually exclusive): (i) conditions causing problems with movement, such as ataxia and (ii) conditions affecting memory and/or related to dementia.

As used herein, the term "inflammatory disease" or "inflammatory disorder" refers to abnormalities associated with inflammation. Inflammation is the complex biological response of vascular tissues to harmful stimuli, such as pathogens, damaged cells, or irritants. It is a protective attempt by the organism to remove the injurious stimuli as well as initiate the healing process for the tissue. However, inflammation which runs unchecked can lead to a host of diseases, such as hay fever, atherosclerosis, and rheumatoid arthritis. The immune system is often involved with inflammatory disorders (such as allergies and cardiomyopathies). There are, however, non-immune diseases with etiological origins in inflammatory processes such as cancer, atherosclerosis, and ischemic heart disease.

A non-limiting list of inflammatory diseases/disorders that can be treated using the method of the present invention includes: Amyotrophic lateral sclerosis (ALS, sometimes called Lou Gehrig's Disease), Alexander disease, Alper's disease, friedereich ataxia, Alzheimer's disease, ataxia telangiectasia, Batten disease (also known as Spielmeyer-Vogt-Sjogren-Batten disease), Canavan disease, Cockayne syndrome, corticobasal degeneration, Creutzfeldt-Jakob disease, Werner syndrome, Huntington's disease, HIV-associated dementia, Kennedy's disease, Krabbe disease, Lewy body dementia, Machado-Joseph disease (Spinocerebellar ataxia type 3), multiple sclerosis, Multiple System Atrophy, Neuroborreliosis, Parkinson's disease, Pelizaeus-Merzbacher Disease, Pick's disease, primary lateral sclerosis , prion diseases, Refsum's disease, Sandhoff disease, Schilder's disease, schizophrenia, spinocerebellar ataxia (multiple types with varying characteristics), spinal muscular atrophy, Steele-Richardson-Olszewski disease, Tabes dorsalis, atherosclerosis, pelvic inflammatory disease (PID), Inflammatory Bowel Disease (IBD), ulcerative colitis (UC), lung inflammatory disease, breast inflammations, inflammatory diseases of the intestine, Rheumatoid Arthritis (RA), Crohn's disease, tuberculosis, inflammatory breast cancer, inflammatory skin disease, and psoriasis.

In therapeutic applications, compositions comprising S16AhTERT or a functional fragment or derivative thereof (or nucleic acid sequences encoding same) are administered to a patient already suffering from a degenerative disorder (such as, e.g., neurodegenerative disorders) in an amount sufficient to cure or at least partially arrest or ameliorate the symptoms of the disease and its complications. An amount adequate to accomplish this is defined as a "therapeutically effective amount or dose." Amounts effective for this use will depend on the severity of the disease and the weight and general state of the patient.

The present invention is applicable to any mammal and thus may be used for veterinary purposes. The high sequence/function conservation observed among species, particularly among mouse, rat and human TERT supports applicability of efficacious use of the S16AhTERT mutant broadly in mammalian species. The subject is preferably an animal, including but not limited to animals such as monkeys, cows, pigs, horses, chickens, cats, dogs, etc., and is particularly a mammal, and more particularly human. In one specific embodiment, a non-human mammal is the subject. In another specific embodiment, a human mammal is the subject.

With respect to targeted delivery of the therapeutic mutant hTERT of the invention, a skilled practitioner can use antibodies, viral infections, the TAT sequence from the HIV virus to target the protein to the nucleus of cells, and nanoparticles to achieve locale specific or localized delivery.

Nanotechnology refers to the use of man-made nano-sized (typically 1-100 billionths of a meter) particles for industrial or medical applications suited to their unique properties. With respect to medical applications, nanoparticles are particles that are a hundred to ten thousand times smaller than human cells. They are similar in size to large biological molecules ("biomolecules") such as enzymes and receptors. Because of their small size, nanoscale devices can readily interact with biomolecules on both the surface and inside of cells. By gaining access to so many areas of the body, they have the potential to detect disease and deliver treatment to virtually any bodily locale.

Many different types of nanoparticles are currently being studied for applications in nanomedicine. They can be carbon-based skeletal-type structures, such as the fullerenes, or micelle-like, lipid-based liposomes, which are already in use for numerous applications in drug delivery and the cosmetic industry. Colloids, typically liposome nanoparticles, selected for their solubility and suspension properties are used in cosmetics, creams, protective coatings and stain-resistant clothing. Other examples of carbon-based nanoparticles are chitosan and alginate-based nanoparticles, which are described in the literature for oral delivery of proteins, and various polymers under study for insulin delivery. Additional nanoparticles can be made from metals and other inorganic materials, such as phosphates. Nanoparticle contrast agents are compounds that enhance magnetic resonance imaging (MRI) and ultrasound results in biomedical applications of in vivo imaging. These particles typically contain metals whose properties are dramatically altered at the nano-scale. Gold "nanoshells" are useful in the fight against cancer, particularly soft-tissue tumors, because of their ability to absorb radiation at certain wavelengths. Once the nanoshells enter tumor cells and radiation treatment is applied, they absorb the energy and heat up enough to kill the cancer cells. Positively-charged silver nanoparticles adsorb onto single-stranded DNA and are used for its detection. Many other tools and devices for in vivo imaging (fluorescence detection systems), and to improve contrast in ultrasound and MRI images, are being developed.

A more detailed description of some nanoparticle types is presented below:

Fullerenes: Buckyballs and Carbon Tubes

Both members of the fullerene structural class, buckyballs and carbon tubes are carbon based, lattice-like, potentially porous molecules. Buckyballs are spherical in shape, while carbon tubes are cylindrical. The diameter of a carbon tube can be several nanometers, but the length can be much greater, up to several millimeters, depending on its intended use. Carbon tubes have many applications in materials science due to their strength and unique electrical properties. They have, however, also found use in the field of biomedicine as carriers for vaccines, drugs and other molecules. A single wall carbon tube is a one-atom-thick sheet of graphite, resembling chicken wire and rolled seamlessly into a tube. There are also multi-walled tubes and other types of tubes depending on the shape, diameter, density (hollow versus solid) and other properties of the tube.

Liposomes

Liposomes are lipid-based nanoparticles used extensively in the pharmaceutical and cosmetic industries because of their capacity to break down inside cells, once their delivery function has been met. Liposomes are the first engineered nanoparticles used for drug delivery, but problems such as their propensity to fuse together in aqueous environments and release their payload, have lead to their replacement or stabilization using newer alternative nanoparticles.

Nanoshells

Also referred to as core-shells, nanoshells are spherical cores of a particular compound surrounded by a shell or outer coating of another, which is a few nanometers thick. One application in biomedicine is to create nanoshells that absorb at biologically useful wavelengths, depending on the shell thickness. One common formula for the construction of nanoshells is to use silica for the core and another sticky compound to adhere gold particles to the outside surface, creating the shell. Nanoshells such as these have been used to kill cancer cells in mice. Once injected into a tumor, radiation is applied and the nanoshells heat up enough to kill the tumor cells.

Dendrimers

Dendrimers are highly branched structures that are gaining wide use in nanomedicine because of the multiple molecular "hooks" on their surfaces that can be used to attach cell-identification tags, fluorescent dyes, enzymes and other molecules. The first dendritic molecules were produced around 1980, but interest in them has blossomed more recently as biotechnological uses are discovered. Nanomedical applications for dendrimers are many and include nanoscale catalysts and reaction vessels, micelle mimics, imaging agents and chemical sensors, and agents for delivering drugs or genes into cells. There are two basic structural types of dendrimers. The first type possesses a globular structure with a central core from which branches radiate. The second type has no central core and consists simply of a series of highly branched polymers.

Quantum Dots

Also known as nanocrystals, quantum dots are nanosized semiconductors that, depending on their size, can emit light in all colors of the rainbow. These nanostructures confine conduction band electrons, valence band holes, or excitons in all three spatial directions. Examples of quantum dots are semiconductor nanocrystals and core-shell nanocrystals, wherein there is an interface between different semiconductor materials. They have been applied in biotechnology for cell labelling and imaging, particularly in cancer imaging studies.

Superparamagnetic Nanoparticles

Superparamagnetic molecules are attracted to a magnetic field, but do not retain residual magnetism after the field is removed. Nanoparticles of iron oxide with diameters in the 5-100 nm range, have been used for selective magnetic bio-separations. Typical techniques involve coating the particles with antibodies to cell-specific antigens, for subsequent separation from the surrounding matrix. Used in membrane transport studies, superparamagenetic iron oxide nanoparticles (SPION) are applied for drug delivery and gene transfection. Targeted delivery of drugs, bioactive molecules or DNA vectors is dependent on the application of an external magnetic force that accelerates and directs their progress towards the target tissue. They are also useful as MRI contrast agents.

Nanorods

Typically 1-100 nm in length, nanorods are most often made from semiconducting materials and used in nanomedicine as imaging and contrast agents. Nanorods can be made by generating small cylinders of silicon, gold or inorganic phosphate, among other materials.

As indicated herein, treatments may be achieved by administering DNA encoding the hTERT mutant of the invention in an expressible genetic construct. DNA encoding the hTERT mutant of the invention may be administered to the patient using techniques known in the art for delivering DNA to the cells. Retroviral vectors, electroporation or liposomes, for example, may be used to deliver DNA.

An "immune response" signifies any reaction produced by an antigen, such as a protein antigen, in a host having a functioning immune system. Immune responses may be either humoral, involving production of immunoglobulins or antibodies, or cellular, involving various types of B and T lymphocytes, dendritic cells, macrophages, antigen presenting cells and the like, or both. Immune responses may also involve the production or elaboration of various effector molecules such as cytokines, lymphokines and the like. Immune responses may be measured both in in vitro and in various cellular or animal systems.

An "antibody" or "antibody molecule" is any immunoglobulin, including antibodies and fragments thereof, that binds to a specific antigen. The term includes polyclonal, monoclonal, chimeric, and bispecific antibodies. As used herein, antibody or antibody molecule contemplates both an intact immunoglobulin molecule and an immunologically active portion of an immunoglobulin molecule such as those portions known in the art as Fab, Fab', F(ab')2 and F(v).

Exemplary epitopes of the mutant hTERT of the present invention that can be used to generate an antibody immunologically specific for the mutant hTERT (i.e., an antibody that only recognizes this mutant) are also encompassed herein. Such an antibody would not, therefore, be immunologically specific for wildtype hTERT or other mutant hTERTs.

hTERT nucleic acids or a fragment thereof comprising such an S16AhTERT mutant specific epitope are also encompassed herein. hTERT nucleic acids or a fragment thereof can comprise a C-terminal Cys or no terminal modifications. Fragments of hTERT include N-terminal fragments [H] and C-terminal fragments [OH].

Immunological purity should be 50% or greater. Antigenic epitopes should, in general, be hydrophilic and have a size range of at least 8 amino acids. Exemplary S16AhTERT mutant specific epitopes are as follows: RAVRSLL-RAHYREV (SEQ ID NO: 7); RSLLRAHY (SEQ ID NO: 8); SLLRAHYRE (SEQ ID NO: 9); LLRAHYREV (SEQ ID NO: 10); LRAHYREVL (SEQ ID NO: 11); and RAHYREVLP (SEQ ID NO: 12).

The term "control substance", "control agent", or "control compound" as used herein refers a molecule that is inert or has no activity relating to an ability to modulate a biological activity. With respect to the present invention, such control substances are inert with respect to an ability to modulate a mutant hTERT activity and/or a signaling pathway that contributes to an activity of a mutant hTERT. Exemplary controls include, but are not limited to, solutions comprising physiological salt concentrations.

"Subject" includes humans. The terms "human," "patient" and "subject" are used interchangeably herein.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

Pharmaceutical Compositions

When employed as pharmaceuticals, the polypeptides of this invention are typically administered in the form of a pharmaceutical composition. Such compositions can be prepared in a manner well known in the pharmaceutical art and comprise at least one active compound.

Generally, the polypeptides of the invention (or DNA encoding a polypeptide of the invention) are administered in a pharmaceutically effective amount. The amount of the polypeptide or DNA encoding same actually administered will typically be determined by a physician, in the light of the relevant circumstances, including the condition to be treated, the chosen route of administration, the actual polypeptide or DNA administered, the age, weight, and response of the individual patient, the severity of the patient's symptoms, and the like.

The pharmaceutical compositions of this invention can be administered by a variety of routes including oral, rectal, transdermal, subcutaneous, intravenous, intramuscular, and intranasal. Depending on the intended route of delivery, the polypeptides of this invention, for example, are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or polypeptides of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration or stability of the active ingredients or the formulation. All such known transdermal formulations and ingredients are included within the scope of this invention.

The polypeptides of this invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

The polypeptides of this invention can also be administered in sustained release forms or from sustained release drug delivery systems. A description of representative sustained release materials can be found in *Remington's Pharmaceutical Sciences.*

The following formulation examples illustrate representative pharmaceutical compositions of this invention. The present invention, however, is not limited to the following pharmaceutical compositions.

Formulation 1—Tablets

A polypeptide of the invention is admixed as a dry powder with a dry gelatin binder in an approximate 1:2 weight ratio. A minor amount of magnesium stearate is added as a lubricant. The mixture is formed into 240-270 mg tablets (80-90 mg of active amide compound per tablet) in a tablet press.

Formulation 2—Capsules

A polypeptide of the invention is admixed as a dry powder with a starch diluent in an approximate 1:1 weight ratio. The mixture is filled into 250 mg capsules (125 mg of active amide compound per capsule).

Formulation 3—Liquid

A polypeptide of the invention (125 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A polypeptide of the invention is admixed as a dry powder with a dry gelatin binder in an approximate 1:2 weight ratio. A minor amount of magnesium stearate is added as a lubricant. The mixture is formed into 450-900 mg tablets (150-300 mg of active amide compound) in a tablet press.

Formulation 5—Injection

A polypeptide of the invention is dissolved or suspended in a buffered sterile saline injectable aqueous medium to a concentration of approximately 5 mg/ml.

Formulation 6—Topical

Stearyl alcohol (250 g) and a white petrolatum (250 g) are melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) is added and the resulting mixture is stirred until it congeals.

Methods of Treatment

The present polypeptides or DNA encoding a polypeptide of the invention are used as therapeutic agents for the treatment of conditions in mammals that are associated with apoptotic cell death, such as degenerative diseases or disorders (e.g., cardiomyopathy, Alzheimer's and Parkinson's disease), telomere shortening/dysfunction (macular degeneration, dyskeratosis congenita), inflammatory conditions/disorders (arthritis) and normal processes of aging. As described herein, the polypeptides of the invention render cells more resistant to oxidative damage and apoptotic death. These properties render susceptible cells more resistant to the toxic effects of oxidative damage. Accordingly, the polypeptides and pharmaceutical compositions of this invention find use as therapeutics for treating a variety of diseases/disorders wherein it is of therapeutic value to increase the resistance of susceptible cells to oxidative stress associated with degenerative diseases or inflammatory conditions in mammals, including humans.

The present invention encompasses treatment of degenerative diseases; diseases that are characterized by the loss of cells (such as neurons); diseases that relate to telomere shortening, such as macular degeneration, arteriosclerosis. cirrhosis of the liver, kidney disease, diabetes, Alzheimer's disease, Parkinson's disease, osteoporosis (any disease that can be treated by lengthening telomeres); and disorders that have an inflammatory component, for example, when oxidative stress caused by inflammation is damaging the cells without killing them. Use of the mutant would help make cells resistant to oxidative damage. Treatment of rare genetic disorders that are believed to originate from defective telomere building, such as progeria or dyskeratosis, are also envisioned. Cosmetic use of mutant telomerase for regenerating skin and reducing wrinkles, stimulation of hair follicle stem cells, hair regrowth, and reverse graying is also intended. Improvements in cell culture technique conferred by expression of the mutant hTERT of the present invention to extend the lifespan of mammalian cell cultures would facilitate screening of more pharmaceutical products or additional assays. The mutant is also useful for preventing or delaying telomere exhaustion in cultures of ex vivo skin and organs for grafting and/or transplantation. Additional applications include increasing the life or healthspan of an organism.

In a method of treatment aspect, this invention provides a method of treating a mammal afflicted with a disease or condition associated with oxidative damage, telomere shortening and/or apoptotic cell death, which method comprises administering an effective amount of one or more of the pharmaceutical compositions just described.

As a further aspect of the invention the present polypeptides are provided for use as a pharmaceutical especially in the treatment of the aforementioned conditions and diseases. Also provided herein is the use of the present polypeptides in the manufacture of a medicament for the treatment of one of the aforementioned conditions and diseases.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the treatment of long-term conditions, such as, for example, arthritis, Parkinson's Disease, and Alzheimer's Disease, the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound of the invention, with preferred doses each providing from about 0.1 to about 10 mg/kg and especially about 1 to about 5 mg/kg.

Transdermal doses are generally selected to provide similar or lower blood levels than are achieved using injection doses.

The polypeptides of this invention can be administered as the sole active agent or they can be administered in combination with other agents, including other polypeptides that demonstrate the same or a similar therapeutic activity, and that are determined to safe and efficacious for such combined administration.

Expression Vectors

A gene encoding an hTERT mutant of the invention, active fragment or derivative thereof, can be introduced either in vivo, ex vivo, or in vitro in a viral vector. Such vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. For example, in the treatment of neurological disorders or injuries, the striatal subventricular zone (SVZ) can be specifically targeted. Examples of particular vectors include, but are not limited to, a defective herpes virus 1 (HSV1) vector (Kaplitt et al., *Molec. Cell. Neurosci.*, 2:320-330 (1991)), an attenuated adenovirus vector, such as the vector described by Stratford-Perricaudet et al. (*J. Clin. Invest.*, 90:626-630 (1992)), and a defective adeno-associated virus vector (Samulski et al., *J. Virol.*, 61:3096-3101 (1987); Samulski et al., *J. Virol.*, 63:3822-3828 (1989)) including a defective adeno-associated virus vector with a tissue specific promoter, (see e.g., U.S. Pat. No. 6,040,172, Issued Mar. 21, 2000, the contents of which are hereby incorporated by reference in their entireties).

In another embodiment, an hTERT mutant of the invention can be introduced in a retroviral vector, e.g., as described in U.S. Pat. No. 5,399,346; Mann et al., (1983) *Cell*, 33:153; U.S. Pat. Nos. 4,650,764; 4,980,289; Markowitz et al., (1988) *J. Virol.*, 62:1120; U.S. Pat. No. 5,124,263; International Patent Publication No. WO 95/07358, published Mar. 16, 1995; and Kuo et al., (1993) *Blood*, 82:845.

Targeted gene delivery is described in International Patent Publication WO 95/28494, published October 1995.

Alternatively, the vector can be introduced by lipofection. Liposomes may be used for encapsulation and transfection of nucleic acids in vitro. Synthetic cationic lipids designed to limit the difficulties and dangers encountered with liposome mediated transfection can be used to prepare liposomes for in vivo transfection of an hTERT mutant of the invention, active fragment or derivative thereof (Felgner, et. al., *Proc. Natl. Acad. Sci. U.S.A.*, 84:7413-7417 (1987); see Mackey, et al., *Proc. Natl. Acad. Sci. U.S.A.*, 85:8027-8031 (1988)). The use of cationic lipids may promote encapsulation of negatively charged nucleic acids, and also promote fusion with negatively charged cell membranes (Felgner and Ringold, *Science*, 337:387-388 (1989)). The use of lipofection to introduce exogenous genes into the specific organs in vivo has certain practical advantages. Molecular targeting of liposomes to specific cells represents one area of benefit. It is clear that directing transfection to particular cell types is particularly advantageous in a tissue with cellular heterogeneity, such as the brain. Lipids may be chemically coupled to other molecules for the purpose of targeting (see Mackey et. al., *Proc. Natl. Acad. Sci. U.S.A.,* 85:8027-8031 (1988)).

It is also possible to introduce the vector as a naked DNA plasmid. Naked DNA vectors for short term or long term gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter (see, e.g., Wu et al., (1992) *J. Biol. Chem.,* 267:963-967; Wu and Wu, (1988) *J. Biol. Chem.,* 263:14621-14624; Hartmut et al., Canadian Patent Application No. 2,012,311, filed Mar. 15, 1990).

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and described the methods and/or materials in connection with which the publications are cited.

Aspects of the Invention

Before the present discovery and methods of use thereof are described, it is to be understood that this invention is not limited to particular assay methods, or test compounds and experimental conditions described, as such methods and compounds may vary. It is also to be understood that the terminology used herein is for the purpose of describing particular embodiments only, and is not intended to be limiting, since the scope of the present invention will be limited only the appended claims.

EXAMPLE I

Nuclear Only Variant

The present inventor previously demonstrated that hTERT localized to the mitochondria drives an enhancement of mitochondrial DNA (mtDNA) damage and apoptosis after hydrogen peroxide treatment ($H_2O_2$). Indeed, by site-directed mutagenesis of the mitochondrial leader sequence of hTERT (substitution of R at positions 3 and 6 for E, R3E/R6EhTERT) the present inventor created a mutant that is only localized to the nucleus and renders cells resistant to both mtDNA damage and apoptosis induced by $H_2O_2$ [Santos et al. (2006) *Hum Mol Genet.* 15, 1757-1768].

It is yet unknown how hTERT's subcellular localization is regulated. The present inventor hypothesized that phosphorylation of hTERT would be one means of regulating hTERT's subcellular compartment. Phosphorylation of hTERT on Y707 had been previously shown to make hTERT shuffle from the nucleus to the cytoplasm after $H_2O_2$ treatment [Haendeler et al. (2003) *Mol Cell Biol.* 13, 4598-610]. Additionally, Semyia and co-workers (EMBO J. 2000 11:2652-61) also demonstrated that the C-terminus of hTERT is phosphorylated by 14-3-3, which regulates its nuclear localization. Finally, phosphorylation of other residues by several different kinases has been demonstrated to play a role in telomerase enzymatic activity and function (Kang et al., (1999) *J. Biol. Chem* 274, 13085-13090; Kim et al., Exp. Mol. Med. 33 (2001), pp. 156-163; Li et al., J Biol Chem. 1997 272:16729-32, Akiyama et al., Cancer Res. 2003 63:18-21, Akiyama et al., Biochem Biophys Res Commun. 2004 316: 528-32).

Accordingly, the present inventor first sought to identify if residues in the mitochondrial leader sequence (MLS) of hTERT (first 20 amino acids) are potential targets of phosphorylation events. For this purpose, the NetPhos 2.0 Software package that predicts phosphorylation sites in a given protein sequence was used. The present inventor identified that serine 16 (S16) had a high probability of being phosphorylated (0.98) using this package. This residue was then mutated to alanine (A) by site-directed mutagenesis to generate S16AhTERT, which was fused to EGFP and expressed transiently in HeLa cells. As can be seen in FIG. 1, while wild type (WT) hTERT localizes to both nucleus and cytoplasm (see inset), S16AhTERT is confined to the nucleus exclusively. These results suggest that S16 is involved in the regulation of hTERT's subcellular localization.

Figure 2:
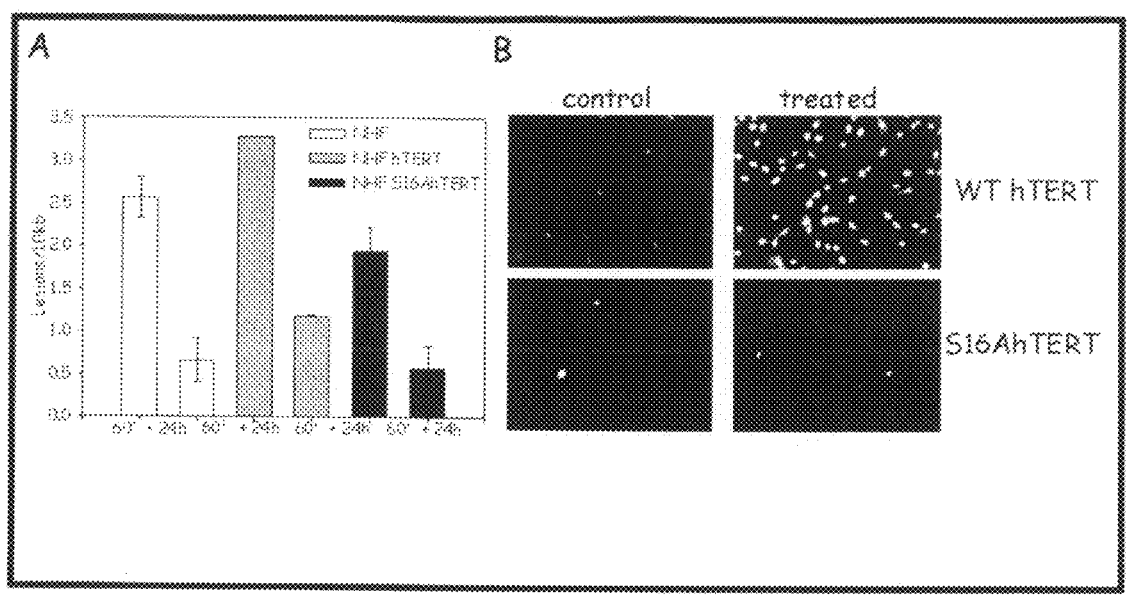
FIG. 2A-B. S16AhTERT makes cells resistant to both mtDNA damage and apoptosis induced by $H_2O_2$. (A) Cells were submitted to 60 min of $H_2O_2$ treatment, and allowed to recover for 24 hours (h). MtDNA integrity was evaluated using quantitative PCR (QPCR) immediately after the treatment and after recovery times. Error bars reflect SEM of two independent experiments. (B) Apoptosis was evaluated 24 h after the treatments by incubation of cells with YOPRO-1, a fluorescent dye specific for apoptotic cells.

The present inventor also expressed this protein stably in NHF cells by cloning S16AhTERT into the pBabe vector. Initial analysis revealed that this protein retains its catalytic activity and immortalizes cells, as characterized by more than 100 population doublings. Moreover, confinement of S16AhTERT only to the nucleus rendered cells resistant to both mtDNA damage as well as apoptosis induced by $H_2O_2$ (FIG. 2A and B).

Discussion

These results demonstrate that localization of hTERT to the nucleus or the mitochondria may be regulated by phosphorylation events in the MLS of hTERT. The results presented in this example demonstrate that substitution of S16 for A, which is predicted to be phosphorylated by an as yet unknown kinase, confines hTERT exclusively to the nucleus. It is yet unknown whether this residue is indeed phosphorylated in vivo, and if so which kinase would be responsible for this activity. Nonetheless, the data presented herein suggest that S16 is involved in the mitochondrial localization of hTERT. Further studies are required to dissect exactly the role of S16 in regulating the subcellular localization of hTERT.

Materials and Methods hTERT constructs. Wild type hTERT and mutant hTERT used in this study were constructed by PCR amplification of hTERT from the hTERT-EGFP vector [Santos et al. (2004) *Aging Cell* 3, 399-411]. Serine 16 was substituted by alanine by site-directed mutagenesis of the above mentioned vector. The above mutation was also introduced into the hTERT-pBabe construct, which had been derived by PCR of the full length hTERT gene using restriction enzymes EcoRI and SalI. The empty retroviral vector pBabe was provided by Dr. Christopher Counter, Duke University. Wild type hTERT-EGFP was described previously vector [Santos et al. (2004) *Aging Cell* 3, 399-411].

Cells and Cell Culture. Primary NHF fibroblasts and the respective hTERT -derivatives were described previously [Santos et al. (2004) *Aging Cell* 3, 399-411]. The pBabe retroviral vector-containing hTERT protein was transfected into the packaging cell line PA317 to produce viruses that were used to infect NHF primary fibroblasts. Control cells were infected with the empty vector. After infection, cells were grown in selection medium containing 2 µg/mL of puromycin for two weeks. Resistant colonies were pooled and tested for telomerase activity as well as immortalization ($\geq$100 population doublings). Cells were routinely grown and sub-cultured as described previously [Santos et al. (2006) *Hum Mol Genet.* 15, 1757-1768]. HeLa cells used for transient transfections were maintained in MEM medium (Gibco) supplemented with 10% FBS and penicillin/streptomycin.

$H_2O_2$ treatments, DNA isolation and analysis of integrity by Quantitative PCR (QPCR). $H_2O_2$ (Sigma) treatments were performed as described earlier [Santos et al. (2003) *J. Biol. Chem.* 278, 1728-1734]. After treatments, cells were washed twice and harvested immediately for DNA analysis. High molecular weight DNA was extracted and QPCR performed and analyzed as described previously [Santos et al. (2002) pp. 159-176 In W. C. Copeland (ed). Methods Mol. Biol.]. Large fragments of both nuclear and mitochondrial genomes were amplified; the primer sequences can be found elsewhere [Santos et al. (2002) pp. 159-176 In W. C. Copeland (ed). Methods Mol. Biol.]. A small (139 bp) fragment of the mtDNA was also amplified, and was used to monitor mitochondrial copy number and to normalize results obtained with the large fragment (for more details see [Santos et al. (2002) pp. 159-176 In W. C. Copeland (ed). Methods Mol. Biol.]).

Telomeric repeat amplification protocol (TRAP). 500 ng of total protein extracts were assayed for telomerase activity using the TRAPeze kit from Chemicon as instructed by the manufacturer and modified as in Santos et al. [(2002) pp. 159-176 In W. C. Copeland (ed). Methods Mol. Biol.].

Apoptosis and cell death/viability assays. YOPRO-1 (Molecular Probes) was used to evaluate the percentage of apoptotic cells in control and treated samples. Cells were analyzed immediately after treatments and 24 h after recovery. During apoptosis the cytoplasmic membrane becomes slightly permeant. Certain dyes, such as the green fluorescent YO-PRO®-1 dye can enter apoptotic cells, whereas other dyes, such as the red fluorescent dye, propidium iodide (PI), cannot. Thus, use of YO-PRO®-1 dye and PI together provide a sensitive indicator for apoptosis [Agrelo et al. (2006) *Proc Natl Acad Sci USA* 103, 8822-8827; Chin et al. (2004) *Nat Genet* 36, 984-988]. Data presented were confirmed with both Hoescht incorporation as well as caspase-3 activation.

The nucleic and amino acid sequences of wild type hTERT and the nuclear only S16AhTERT mutant are presented below:

```
DNA sequence of wild type hTERT
                                                                                  (SEQ ID NO: 3)
atgccgcgcgctccccgctgccgagccgtgcgctccctgctgcgcagccactaccgcgaggtgctgccgctggccacgttcgt gcggcgcctggggcccagggctggcggctggtgcagcgcggggacccggcggctttccgcgcgctggtggcccagtgcc tggtgtgcgtgccctgggacgcacggccgcccccgccgcccctccttccgccaggtgtcctgcctgaaggagctggtggc ccgagtgctgcagaggctgtgcgagcgcggcgcgaagaacgtgctggccttcggcttcgcgctgctggacggggcccgcgg gggccccccgaggccttcaccaccagcgtgcgcagctacctgcccaacacggtgaccgacgcactgcggggggagcgggg cgtgggggctgctgctgcgccgcgtgggcgacgacgtgctggttcacctgctggcacgctgcgcgctctttgtgctggtggctc ccagctgcgcctaccaggtgtgcgggccgccgctgtaccagctcggcgctgccactcaggcccggcccccgccacacgcta gtggaccccgaaggcgtctgggatgcgaacgggcctggaaccatagcgtcagggaggccggggtcccctgggcctgcca gccccgggtgcgaggaggcgcggggcagtgccagccgaagtctgccgttgcccaagaggcccaggcgtggcgctgccc ctgagccggagcggacgcccgttgggcaggggtcctgggcccacccgggcaggacgcgtggaccgagtgaccgtggtttct gtgtggtgtcacctgccagacccgccgaagaagccacctctttggagggtgcgctctctggcacgcgccactcccacccatcc gtgggccgccagcaccacgcgggccccccatccacatcgcggccaccacgtccctgggacacgccttgtccccggtgtac gccgagaccaagcacttcctctactcctcaggcgacaaggagcagctgcggccctccttcctactcagctctctgaggcccagc ctgactggcgctcggaggctcgtggagaccatctttctgggttccaggccctggatgccagggactccccgcaggttgccccg cctgcccagcgctactggcaaatgcggcccctgtttctggagctgcttgggaaccacgcgcagtgcccctacggggtgctcct caagacgcactgcccgctgcgagctgcggtcacccagcagccggtgtctgtgcccgggagaagcccagggctctgtggc ggcccccgaggaggaggacacagacccccgtcgcctggtgcagctgctccgccagcacagcagccctggcaggtgtacg gcttcgtgcgggcctgcctgcgccggctggtgccccaggcctctggggctccaggcacaacgaacgccgcttcctcaggaa caccaagaagttcatctccctggggaagcatgccaagctctcgctgcaggagctgacgtggaagatgagcgtgcgggactgc gcttggctgcgcaggagcccaggggttggctgtgttccggccgcagagcaccgtctgcgtgaggagatcctggccaagttcct gcactggctgatgagtgtgtacgtcgtcgagctgctcaggtctttcttttatgtcacggagaccacgtttcaaaagaacaggctcttt ttctaccggaagagtgtctggagcaagttgcaaagcattggaatcagacagcacttgaagaggtgcagctgcgggagctgtc ggaagcagaggtcaggcagcatcgggaagccaggcccgccctgctgacgtccagactccgcttcatcccaagcctgacgg gctgcggccgattgtgaacatggactacgtcgtgggagccagaacgttccgcagagaaaagagggccgagcgtctcacctcg agggtgaaggcactgttcagcgtgctcaactacgagcgggcgcggcgccccggcctcctgggcgcctctgtgctgggcctgg acgatatccacagggcctggcgcaccttcgtgctgcgtgtgcgggcccaggacccgccgcctgagctgtactttgtcaaggtg gatgtgacgggcgcgtacgacaccatcccccaggacaggctcacggaggtcatcgccagcatcatcaaacccagaacacgt actgcgtgcgtcggtatgccgtggtccagaaggccgcccatgggcacgtccgcaaggccttcaagagccacgtctctaccttg acagacctccagccgtacatgcgacagttcgtggctcacctgcaggagaccagcccgctgagggatgccgtcgtcatcgagc
```

-continued agagctcctccctgaatgaggccagcagtggcctcttcgacgtcttcctacgcttcatgtgccaccacgccgtgcgcatcaggg gcaagtcctacgtccagtgccaggggatcccgcagggctccatcctctccacgctgctctgcagcctgtgctacggcgacatgg agaacaagctgtttgcggggattcggcgggacgggctgctcctgcgtttggtggatgatttcttgttggtgacacctcacctcacc cacgcgaaaaccttcctcaggaccctggtccgaggtgtccctgagtatggctgcgtggtgaacttgcggaagacagtggtgaac ttccctgtagaagacgaggccctgggtggcacggcttttgttcagatgccggcccacggcctattccctggtgcggcctgctgc tggatacccggaccctggaggtgcagagcgactactccagctatgcccggacctccatcagagccagtctcaccttcaaccgc ggcttcaaggctgggaggaacatgcgtcgcaaactctttggggtcttgcggctgaagtgtcacagcctgtttctggatttgcaggt gaacagcctccagacggtgtgcaccaacatctacaagatcctcctgctgcaggcgtacaggtttcacgcatgtgtgctgcagctc ccatttcatcagcaagtttggaagaaccccacattttcctgcgcgtcatctctgacacggcctccctctgctactccatcctgaaag ccaagaacgcagggatgtcgctgggggccaagggcgccgccggccctctgccctccgaggccgtgcagtggctgtgccacc aagcattcctgctcaagctgactcgacaccgtgtgcacctacgtgccactcctggggtcactcaggacagcccagacgcagctga gtcggaagctcccggggacgacgctgactgccctggaggccgcagccaacccggcactgccctcagacttcaagaccatcct ggac Amino acid sequence of wild type hTERT (SEQ ID NO: 4)

MPRAPRCRAVRSLLRSHYREVLPLATFVRRLGPQGWRLVQRGDPAAFRALVAQ

CLVCVPWDARPPPAAPSFRQVSCLKELVARVLQRLCERGAKNVLAFGFALLDGA

RGGPPEAFTTSVRSYLPNTVTDALRGSGAWGLLLRRVGDDVLVHLLARCALFVL

VAPSCAYQVCGPPLYQLGAATQARPPPHASGPRRRLGCERAWNHSVREAGVPL

GLPAPGARRRGGSASRSLPLPKRPRRGAAPEPERTPVGQGSWAHPGRTRGPSDR

GFCVVSPARPAEEATSLEGALSGTRHSHPSVGRQHHAGPPSTSRPPRPWDTPCPP

VYAETKHFLYSSGDKEQLRPSFLLSSLRPSLTGARRLVETIFLGSRPWMPGTPRRL

PRLPQRYWQMRPLFLELLGNHAQCPYGVLLKTHCPLRAAVTPAAGVCAREKPQ

GSVAAPEEEDTDPRRLVQLLRQHSSPWQVYGFVRACLRRLVPPGLWGSRHNER

RFLRNTKKFISLGKHAKLSLQELTWKMSVRDCAWLRRSPGVGCVPAAEHRLREE

ILAKFLHWLMSVYVVELLRSFFYVTETTFQKNRLFFYRKSVWSKLQSIGIRQHLK

RVQLRELSEAEVRQHREARPALLTSRLRFIPKPDGLRPIVNMDYVVGARTFRREK

RAERLTSRVKALFSVLNYERARRPGLLGASVLGLDDIHRAWRTFVLRVRAQDPP

PELYFVKVDVTGAYDTIPQDRLTEVIASIIKPQNTYCVRRYAVVQKAAHGHVRK

AFKSHVSTLTDLQPYMRQFVAHLQETSPLRDAVVIEQSSSLNEASSGLFDVFLRF

MCHHAVRIRGKSYVQCQGIPQGSILSTLLCSLCYGDMENKLFAGIRRDGLLLRLV

DDFLLVTPHLTHAKTFLRTLVRGVPEYGCVVNLRKTVVNFPVEDEALGGTAFVQ

MPAHGLFPWCGLLLDTRTLEVQSDYSSYARTSIRASLTFNRGFKAGRNMRRKLF

GVLRLKCHSLFLDLQVNSLQTVCTNIYKILLLQAYRFHACVLQLPFHQQVWKNP

TFFLRVISDTASLCYSILKAKNAGMSLGAKGAAGPLPSEAVQWLCHQAFLLKLT

RHRVTYVPLLGSLRTAQTQLSRKLPGTTLTALEAAANPALPSDFKTILD

DNA sequence of nuclear only hTERT. (S16AhTERT; SEQ ID NO: 1)

ATGCCGCGCGCTCCCCGCTGCCGAGCCGTGCGCTCCCTGCTGCGCGCCCACTA

CCGCGAGGTGCTGCCGCTGGCCACGTTCGTGCGGCGCCTGGGGCCCCAGGGC

TGGCGGCTGGTGCAGCGCGGGGACCCGGCGGCTTTCCGCGCGCTGGTGGCCC

AGTGCCTGGTGTGCGTGCCCTGGGACGCACGGCCGCCCCCCGCCGCCCCCTC

CTTCCGCCAGGTGTCCTGCCTGAAGGAGCTGGTGGCCCGAGTGCTGCAGAGG

-continued

```
CTGTGCGAGCGCGGCGCGAAGAACGTGCTGGCCTTCGGCTTCGCGCTGCTGG

ACGGGGCCCGCGGGGGCCCCCCCGAGGCCTTCACCACCAGCGTGCGCAGCTA

CCTGCCCAACACGGTGACCGACGCACTGCGGGGGAGCGGGGCGTGGGGGCT

GCTGCTGCGCCGCGTGGGCGACGACGTGCTGGTTCACCTGCTGGCACGCTGC

GCGCTCTTTGTGCTGGTGGCTCCCAGCTGCGCCTACCAGGTGTGCGGGCCGCC

GCTGTACCAGCTCGGCGCTGCCACTCAGGCCCGGCCCCCGCCACACGCTAGT

GGACCCCGAAGGCGTCTGGGATGCGAACGGGCCTGGAACCATAGCGTCAGG

GAGGCCGGGTCCCCCTGGGCCTGCCAGCCCCGGGTGCGAGGAGGCGCGGG

GGCAGTGCCAGCCGAAGTCTGCCGTTGCCCAAGAGGCCCAGGCGTGGCGCTG

CCCCTGAGCCGGAGCGGACGCCCGTTGGGCAGGGGTCCTGGGCCCACCCGGG

CAGGACGCGTGGACCGAGTGACCGTGGTTTCTGTGTGGTGTCACCTGCCAGA

CCCGCCGAAGAAGCCACCTCTTTGGAGGGTGCGCTCTCTGGCACGCGCCACT

CCCACCCATCCGTGGGCCGCCAGCACCACGCGGGCCCCCCATCCACATCGCG

GCCACCACGTCCCTGGGACACGCCTTGTCCCCCGGTGTACGCCGAGACCAAG

CACTTCCTCTACTCCTCAGGCGACAAGGAGCAGCTGCGGCCCTCCTTCCTACT

CAGCTCTCTGAGGCCCAGCCTGACTGGCGCTCGGAGGCTCGTGGAGACCATC

TTTCTGGGTTCCAGGCCCTGGATGCCAGGGACTCCCCGCAGGTTGCCCCGCCT

GCCCCAGCGCTACTGGCAAATGCGGCCCCTGTTTCTGGAGCTGCTTGGGAAC

CACGCGCAGTGCCCCTACGGGGTGCTCCTCAAGACGCACTGCCCGCTGCGAG

CTGCGGTCACCCCAGCAGCCGGTGTCTGTGCCCGGGAGAAGCCCCAGGGCTC

TGTGGCGGCCCCCGAGGAGGAGGACACAGACCCCCGTCGCCTGGTGCAGCTG

CTCCGCCAGCACAGCAGCCCCTGGCAGGTGTACGGCTTCGTGCGGGCCTGCC

TGCGCCGGCTGGTGCCCCAGGCCTCTGGGGCTCCAGGCACAACGAACGCCG

CTTCCTCAGGAACACCAAGAAGTTCATCTCCCTGGGGAAGCATGCCAAGCTC

TCGCTGCAGGAGCTGACGTGGAAGATGAGCGTGCGGGACTGCGCTTGGCTGC

GCAGGAGCCCAGGGGTTGGCTGTGTTCCGGCCGCAGAGCACCGTCTGCGTGA

GGAGATCCTGGCCAAGTTCCTGCACTGGCTGATGAGTGTGTACGTCGTCGAG

CTGCTCAGGTCTTTCTTTTATGTCACGGAGACCACGTTTCAAAAGAACAGGCT

CTTTTTCTACCGGAAGAGTGTCTGGAGCAAGTTGCAAAGCATTGGAATCAGA

CAGCACTTGAAGAGGGTGCAGCTGCGGGAGCTGTCGGAAGCAGAGGTCAGG

CAGCATCGGGAAGCCAGGCCCGCCCTGCTGACGTCCAGACTCCGCTTCATCC

CCAAGCCTGACGGGCTGCGGCCGATTGTGAACATGGACTACGTCGTGGGAGC

CAGAACGTTCCGCAGAGAAAAGAGGGCCGAGCGTCTCACCTCGAGGGTGAA

GGCACTGTTCAGCGTGCTCAACTACGAGCGGGCGCGGCGCCCCGGCCTCCTG

GGCGCCTCTGTGCTGGGCCTGGACGATATCCACAGGGCCTGGCGCACCTTCG

TGCTGCGTGTGCGGGCCCAGGACCCGCCGCCTGAGCTGTACTTTGTCAAGGT

GGATGTGACGGGCGCGTACGACACCATCCCCCAGGACAGGCTCACGGAGGTC

ATCGCCAGCATCATCAAACCCCAGAACACGTACTGCGTGCGTCGGTATGCCG

TGGTCCAGAAGGCCGCCCATGGGCACGTCCGCAAGGCCTTCAAGAGCCACGT

CTCTACCTTGACAGACCTCCAGCCGTACATGCGACAGTTCGTGGCTCACCTGC
```

```
AGGAGACCAGCCCGCTGAGGGATGCCGTCGTCATCGAGCAGAGCTCCTCCCT

GAATGAGGCCAGCAGTGGCCTCTTCGACGTCTTCCTACGCTTCATGTGCCACC

ACGCCGTGCGCATCAGGGGCAAGTCCTACGTCCAGTGCCAGGGGATCCCGCA

GGGCTCCATCCTCTCCACGCTGCTCTGCAGCCTGTGCTACGGCGACATGGAG

AACAAGCTGTTTGCGGGGATTCGGCGGGACGGGCTGCTCCTGCGTTTGGTGG

ATGATTTCTTGTTGGTGACACCTCACCTCACCCACGCGAAAACCTTCCTCAGG

ACCCTGGTCCGAGGTGTCCCTGAGTATGGCTGCGTGGTGAACTTGCGGAAGA

CAGTGGTGAACTTCCCTGTAGAAGACGAGGCCCTGGGTGGCACGGCTTTTGT

TCAGATGCCGGCCCACGGCCTATTCCCCTGGTGCGGCCTGCTGCTGGATACCC

GGACCCTGGAGGTGCAGAGCGACTACTCCAGCTATGCCCGGACCTCCATCAG

AGCCAGTCTCACCTTCAACCGCGGCTTCAAGGCTGGGAGGAACATGCGTCGC

AAACTCTTTGGGGTCTTGCGGCTGAAGTGTCACAGCCTGTTTCTGGATTTGCA

GGTGAACAGCCTCCAGACGGTGTGCACCAACATCTACAAGATCCTCCTGCTG

CAGGCGTACAGGTTTCACGCATGTGTGCTGCAGCTCCCATTTCATCAGCAAGT

TTGGAAGAACCCCACATTTTTCCTGCGCGTCATCTCTGACACGGCCTCCCTCT

GCTACTCCATCCTGAAAGCCAAGAACGCAGGGATGTCGCTGGGGGCCAAGG

GCGCCGCCGGCCCTCTGCCCTCCGAGGCCGTGCAGTGGCTGTGCCACCAAGC

ATTCCTGCTCAAGCTGACTCGACACCGTGTCACCTACGTGCCACTCCTGGGGT

CACTCAGGACAGCCCAGACGCAGCTGAGTCGGAAGCTCCCGGGGACGACGC

TGACTGCCCTGGAGGCCGCAGCCAACCCGGCACTGCCCTCAGACTTCAAGAC

CATCCTGGAC.
```

Amino acid sequence of nuclear only hTERT. The
mutation is underlined.

(S16AhTERT; SEQ ID NO: 2)

MPRAPRCRAVRSLLR<u>A</u>HYREVLPLATFVRRLGPQGWRLVQRGDPAAFRALVAQ

CLVCVPWDARPPPAAPSFRQVSCLKELVARVLQRLCERGAKNVLAFGFALLDGA

RGGPPEAFTTSVRSYLPNTVTDALRGSGAWGLLLRRVGDDVLVHLLARCALFVL

VAPSCAYQVCGPPLYQLGAATQARPPPHASGPRRRLGCERAWNHSVREAGVPL

GLPAPGARRRGGSASRSLPLPKRPRRGAAPEPERTPVGQGSWAHPGRTRGPSDR

GFCVVSPARPAEEATSLEGALSGTRHSHPSVGRQHHAGPPSTSRPPRPWDTPCPP

VYAETKHFLYSSGDKEQLRPSFLLSSLRPSLTGARRLVETIFLGSRPWMPGTPRRL

PRLPQRYWQMRPLFLELLGNHAQCPYGVLLKTHCPLRAAVTPAAGVCAREKPQ

GSVAAPEEEDTDPRRLVQLLRQHSSPWQVYGFVRACLRRLVPPGLWGSRHNER

RFLRNTKKFISLGKHAKLSLQELTWKMSVRDCAWLRRSPGVGCVPAAEHRLREE

ILAKFLHWLMSVYVVELLRSFFYVTETTFQKNRLFFYRKSVWSKLQSIGIRQHLK

RVQLRELSEAEVRQHREARPALLTSRLRFIPKPDGLRPIVNMDYVVGARTFRREK

RAERLTSRVKALFSVLNYERARRPGLLGASVLGLDDIHRAWRTFVLRVRAQDPP

PELYFVKVDVTGAYDTIPQDRLTEVIASIIKPQNTYCVRRYAVVQKAAHGHVRK

AFKSHVSTLTDLQPYMRQFVAHLQETSPLRDAVVIEQSSSLNEASSGLFDVFLRF

MCHHAVRIRGKSYVQCQGIPQGSILSTLLCSLCYGDMENKLFAGIRRDGLLLRLV

DDFLLVTPHLTHAKTFLRTLVRGVPEYGCVVNLRKTVVNFPVEDEALGGTAFVQ

MPAHGLFPWCGLLLDTRTLEVQSDYSSYARTSIRASLTFNRGFKAGRNMRRKLF

GVLRLKCHSLFLDLQVNSLQTVCTNIYKILLLQAYRFHACVLQLPFHQQVWKNP

TFFLRVISDTASLCYSILKAKNAGMSLGAKGAAGPLPSEAVQWLCHQAFLLKLT

RHRVTYVPLLGSLRTAQTQLSRKLPGTTLTALEAAANPALPSDFKTILD

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. An isolated polypeptide comprising SEQ ID NO: 2, wherein said isolated polypeptide renders cells more resistant to oxidative damage and apoptotic death and extends telomeres in the absence of mitochondrial sensitization.

2. An isolated antibody immunologically specific for the amino acid sequence comprising SEQ ID NO: 2.

3. The antibody of claim 2, wherein said antibody is a polyclonal antibody.

4. The antibody of claim 2, wherein said antibody is a monoclonal antibody.

5. A composition comprising the isolated polypeptide of claim 1 and a pharmaceutical excipient.

6. A kit comprising the isolated polypeptide of claim 1, a buffer compatible with an activity of the isolated polypeptide of claim 1, and instructional materials.

7. A method for promoting cellular resistance to oxidative damage and apoptotic death and telomere extension in the absence of mitochondrial sensitization, said method comprising cloning and expressing a polypeptide comprising SEQ ID NO: 2 in a cell, wherein the cell is in vitro or in vivo non-human animal cell, wherein expression of said polypeptide promotes cellular resistance to oxidative damage and apoptotic death and telomere extension in the absence of mitochondrial sensitization in the cell relative to a control cell wherein said polypeptide is not expressed.

8. The method of claim 7, wherein the cell is in vitro.

9. The method of claim 7, wherein the cell is in vivo non-human animal cell.

* * * * *